(12) United States Patent
Weiss et al.

(10) Patent No.: US 10,842,913 B2
(45) Date of Patent: Nov. 24, 2020

(54) SCALABLE THREE-DIMENSIONAL ELASTIC CONSTRUCT MANUFACTURING

(71) Applicant: ALLERGAN PHARMACEUTICALS INTERNATIONAL LIMITED, Dublin (IE)

(72) Inventors: Anthony Steven Weiss, Sydney (AU); Suzanne Marie Mithieux, Sydney (AU)

(73) Assignee: ALLERGAN PHARMACEUTICALS INTERNATIONAL LIMITED, Dublin (IE)

( * ) Notice: Subject to any disclaimer, the term of this patent is extended or adjusted under 35 U.S.C. 154(b) by 232 days.

(21) Appl. No.: 14/650,542

(22) PCT Filed: Dec. 10, 2013

(86) PCT No.: PCT/AU2013/001435
§ 371 (c)(1),
(2) Date: Jun. 8, 2015

(87) PCT Pub. No.: WO2014/089610
PCT Pub. Date: Jun. 19, 2014

(65) Prior Publication Data
US 2016/0067741 A1 Mar. 10, 2016

(30) Foreign Application Priority Data
Dec. 10, 2012 (AU) ................ 2012905409

(51) Int. Cl.
| | | |
|---|---|---|
| A61L 27/22 | (2006.01) | |
| C07K 14/78 | (2006.01) | |
| A61L 27/52 | (2006.01) | |
| B05D 3/00 | (2006.01) | |
| C09D 189/00 | (2006.01) | |
| A61K 38/00 | (2006.01) | |

(52) U.S. Cl.
CPC ............ *A61L 27/22* (2013.01); *A61L 27/227* (2013.01); *A61L 27/52* (2013.01); *B05D 3/007* (2013.01); *C07K 14/78* (2013.01); *C09D 189/00* (2013.01); *A61K 38/00* (2013.01)

(58) Field of Classification Search
CPC ...................................................... A61L 27/22
USPC ....................................................... 427/330
See application file for complete search history.

(56) References Cited

U.S. PATENT DOCUMENTS

| | | | |
|---|---|---|---|
| 4,947,840 A | 8/1990 | Yannas et al. | |
| 5,260,203 A | 11/1993 | Ladner et al. | |
| 6,248,516 B1 | 6/2001 | Winter et al. | |
| 7,001,328 B1 | 2/2006 | Barofsky | |
| 7,125,960 B2 * | 10/2006 | Keiichi ................... | C08H 1/06 424/422 |
| 7,618,935 B2 | 11/2009 | Hill et al. | |
| 7,700,126 B2 | 4/2010 | Ng et al. | |
| 8,038,991 B1 | 10/2011 | Stankus et al. | |
| 8,101,717 B2 | 1/2012 | Weiss et al. | |
| 8,383,158 B2 | 2/2013 | Michal et al. | |
| 8,518,105 B2 | 8/2013 | Hossainy et al. | |
| 2002/0150564 A1 | 10/2002 | Ensley | |
| 2003/0166848 A1 | 9/2003 | Rothstein | |
| 2004/0110439 A1 | 6/2004 | Chaikof et al. | |
| 2004/0136977 A1 * | 7/2004 | Miyamoto ............ | A61L 27/227 424/94.63 |
| 2004/0253220 A1 | 12/2004 | Perrier et al. | |
| 2004/0258676 A1 | 12/2004 | Perrier et al. | |
| 2004/0267362 A1 | 12/2004 | Hwang et al. | |
| 2005/0244393 A1 | 11/2005 | Phillipapart et al. | |
| 2006/0115457 A1 | 6/2006 | Hnojewyj | |
| 2007/0005148 A1 | 4/2007 | Barofsky | |
| 2007/0237735 A1 | 10/2007 | Denommee et al. | |
| 2007/0287741 A1 | 12/2007 | Herzberg et al. | |
| 2008/0107708 A1 | 5/2008 | Ng et al. | |
| 2009/0035251 A1 | 2/2009 | Wortzman et al. | |
| 2009/0169593 A1 | 7/2009 | Gregory et al. | |
| 2009/0226519 A1 | 9/2009 | Claude et al. | |
| 2010/0004699 A1 | 1/2010 | Alleyne et al. | |
| 2010/0021440 A1 * | 1/2010 | Weiss ...................... | A61K 8/64 424/93.7 |
| 2010/0040710 A1 | 2/2010 | Perrier et al. | |
| 2010/0159008 A1 | 6/2010 | Barron et al. | |
| 2010/0247454 A1 | 9/2010 | Mitts et al. | |

(Continued)

FOREIGN PATENT DOCUMENTS

| | | |
|---|---|---|
| EP | 0210846 | 2/1987 |
| EP | 0480048 | 4/1992 |

(Continued)

OTHER PUBLICATIONS

Hu, Biomaterials Derived from Silk-Tropoelastin Protein Systems, Biomaterials, Nov. 2010; 31(32): p. 8121-8131 (Year: 2010).*
Akhtar et al. (2010) "Oxidative and Nitrosative Modifications of Tropoelastin Prevent Elastic Fiber Assembly in Vitro," J. Biol. Chem., 285: 37396-37404.
Albertine et al. (2010) "Chronic lung disease in preterm lambs: effect of daily vitamin A treatment on alveolarization," Am J. Physiol Lung Cell Mol., 299(1): 59-72.
Almine et al. (2012) "Elastin Signaling in Wound Repair" Birth Defects Research, 96:248-257.
Amann and Brosius (1985) "'ATG vectors' for regulated high-level expression of cloned genes in *Escherichia coli*" Gene, 40:183-190.
Annabi et al. (2009) "The fabrication of elastin-based hydrogels using high pressure CO2" Biomaterials, 30:1-7.

(Continued)

*Primary Examiner* — Tabatha L Penny
(74) *Attorney, Agent, or Firm* — Nathan S. Smith; Christopher J. Betti; Morgan, Lewis & Bockius LLP

(57) ABSTRACT

Tissue repair and restoration can be performed using an elastic material formed from tropoelastin. The elastic material can be formed by providing a solution of tropoelastin monomers, applying the solution to a surface, and heating the solution on the surface in absence of a cross-linking agent to enable the tropoelastin monomers to bind to each other to form an elastic material that does not dissociate into tropoelastin monomers when the elastic material is contacted with an aqueous solution.

38 Claims, 10 Drawing Sheets
Specification includes a Sequence Listing.

(56) References Cited

U.S. PATENT DOCUMENTS

| | | | |
|---|---|---|---|
| 2011/0223230 | A1 | 9/2011 | Hersel et al. |
| 2011/0229574 | A1 | 9/2011 | Guillen |
| 2012/0021063 | A1* | 1/2012 | Matsumoto ............ A61L 27/26 424/602 |
| 2012/0220691 | A1 | 8/2012 | Shreiber et al. |
| 2013/0071500 | A1 | 3/2013 | Kizoulis et al. |
| 2013/0164340 | A1 | 6/2013 | Ensley et al. |
| 2013/0296528 | A1 | 11/2013 | Sommer-Knudsen |

FOREIGN PATENT DOCUMENTS

| | | |
|---|---|---|
| JP | 2008-291258 | 12/2008 |
| JP | 2009-512508 | 3/2009 |
| WO | WO 1994007921 | 4/1994 |
| WO | WO 1994014958 | 7/1994 |
| WO | 1998006830 | 2/1998 |
| WO | 1998/034563 | 8/1998 |
| WO | WO 1998044001 | 10/1998 |
| WO | WO 1999003886 | 1/1999 |
| WO | WO 1999011196 | 3/1999 |
| WO | WO 2000004043 | 1/2000 |
| WO | WO 2000073399 | 12/2000 |
| WO | WO 2001036000 | 5/2001 |
| WO | WO 2001056595 | 8/2001 |
| WO | WO 2004091592 | 10/2004 |
| WO | WO 2006101441 | 9/2006 |
| WO | 2007/029913 | 3/2007 |
| WO | WO 2007/048115 | 4/2007 |
| WO | 2008/033847 | 3/2008 |
| WO | 2008037028 | 4/2008 |
| WO | WO 2008058323 | 5/2008 |
| WO | WO 2009015372 | 1/2009 |
| WO | WO 2009034559 | 3/2009 |
| WO | 2009/099570 | 8/2009 |
| WO | 2009098024 | 8/2009 |
| WO | WO 2010102337 | 9/2010 |
| WO | 2011/127478 | 10/2011 |
| WO | WO 2012068619 | 5/2012 |
| WO | 2012/080706 | 6/2012 |
| WO | WO 2013044314 | 4/2013 |
| WO | WO 2014063194 | 5/2014 |
| WO | WO 2015021508 | 2/2015 |
| WO | WO 2015042639 | 4/2015 |
| WO | WO-2008/020329 A2 | 2/2018 |

OTHER PUBLICATIONS

Annabi et al. (2009) "Synthesis of highly porous crosslinked elastin hydrogels and their interaction with fibroblasts in vitro" Biomaterials, 30:4550-4557.
Annabi et al. (2010) "Cross-linked open-pore elastic hydrogels based on tropoelastin, elastin and high pressure CO2" Biomaterials, 31:1655-1665.
Aubin et al. (2010) "Directed 3D cell alignment and elongation in microengineered hydrogels" Biomaterials, 31:6941-6951.
Ayres et al. (2003) "Elastin-Based Side Chain Polymers Synthesized by ATRP" Macromolecules 36:5967-5973.
Ayres et al. (2005) "Stimulus Responsive Behavior of Elastin-Based Side Chain Polymers" Macromolecules 38:1699-1704.
Baar et al. (2005) "Self-organization of rat cardiac cells into contractile 3-D cardiac tissue" The FASEB Journal, 19:275-277.
Bae et al. (2011) "Cell-laden microengineered pullulan methacrylate hydrogels promote cell proliferation and 3D cluster formation" Soft Matter, 7:1903-1911.
Bax et al. (2009) "Cell Adhesion to Tropoelastin Is Mediated via the C-terminal GRKRK Motif and Integrin" Journal of Biological Chemistry, 284(42):28616-28623.
Bellingham et al. (2003) "Recombinant Human Elastin Polypeptides Self-Assemble into Biomaterials with Elastin-Like Properties" Biopolymers, 70:445-455.
Bjellqvist et al. (1993) "A nonlinear wide-range immobilized pH gradient for two-dimensional electrophoresis and its definition in a relevant pH scale" Electrophoresis, 14:1357-1365.

Boateng et al. (2005) "RGD and YIGSR synthetic peptides facilitate cellular adhesion identical to that of laminin and fibronectin but alter the physiology of neonatal cardiac myocytes" American Journal of Physiology—Cell Physiology, 288:C30-C38.
Brammer et al. (2009) "Improved bone-forming functionality on diameter-controlled TiO2 nanotube surface" Acta Biomaterialia, 5:3215-3223.
Cenizo et al. (2006) "LOXL as a target to increase the elastin content in adult skin: a dill extract induces the LOXL gene expression," Exp Dermatol., 15(8): 574-581.
Charest et al. (2007) "Myoblast alignment and differentiation on cell culture substrates with microscale topography and model chemistries" Biomaterials, 28:2202-2210.
Chen et al. (2009) "Fibulin-4 regulates expression of the tropoelastin gene and consequent elastic-fibre formation by human fibroblasts,"J. Biochem., 423: 79-89.
Chung and Miller (1988) "A rapid and convenient method for the preparation and storage of competent bacterial cells" Nucleic Acids Res., 16(8):3580.
Cleary and Gibson (1996) "Elastic Tissue, Elastin and Elastin Associated Microfibrils" Extracellular Matrix, vol. 2 p. 95.
Eastoe (1955) "The Amino Acid Composition of Mammalian Collagen and Gelatin" Biochemical Journal, 61:589-600.
Feinberg et al. (2007) "Muscular Thin Films for Building Actuators and Powering Devices" Science, 317:1366-1370.
Fornieri et al. (1987) "Lysyl Oxidase Activity and Elastin/ Glycosaminoglycan Interactions in Growing Chick and Rat Aortas" J. of Cell Biology, 105:1463-1469.
Giraud et al. (2007) "Current State of the Art in Myocardial Tissue Engineering" Tissue Engineering, 13(8):1825-1836.
Hædersdal et al. (2010) "Fractional CO2 Laser Assisted Drug Delivery" Lasers in Surgery and Medicine, 42:113-122.
Hashimoto et al. (2004) "Development of alginate wound dressings linked with hybrid peptides derived from laminin and elastin" Biomaterials, 25:1407-1414.
Hill et al. (2004) "cpnDB: A Chaperonin Sequence Database" Genome Res. 14:1669-1675.
Huang et al. (2006) "Inhibition of Versican Synthesis by Antisense Alters Smooth Muscle Cell Phenotype and Induces Elastic Fiber Formation In Vitro and in Neointima After Vessel Injury," Circ. Res., 98(3):370-377.
Hwang et al. (2008) "Retrovirally Mediated Overexpression of Glycosaminoglycan-Deficient Biglycan in Arterial Smooth Muscle Cells Induces Tropoelastin Synthesis and Elastic Fiber Formation In Vitro and in Neointimae after Vascular Injury," Am J Pathol., 173(6):1919-1928.
Jin et al. (2010) "Synthesis and characterization of hyaluronic acid-poly(ethylene glycol) hydrogels via Michael addition: An injectable biomaterial for cartilage repair" Acta Biomaterialia, 6:1968-1977.
Kalluri et al. (2011) "Characterization of microchannels created by metal microneedles: formation and closure," AAPS J.,13:4473-4481.
Kanematsu et al. (2004) "Collagenous matrices as release carriers of exogenous growth factors" Biomaterials, 25:4513-4520.
Kellouche et al. (2007) "Tissue engineering for fullthickness burns: A dermal substitute from bench to bedside" Biochem. and Biophysical Res. Comm. 363:472-478.
Kozel et al. (2006) "Elastic fiber formation: a dynamic view of extracellular matrix assembly using timer reporters," J Cell Physiol. 207:87-96.
Lanasa et al. (2009) "Influence of ECM proteins and their analogs on cells cultured on 2-D hydrogels for cardiac muscle tissue engineering" Acta Biomaterialia, 5:2929-2938.
Mahoney et al. (2009) "Extracellular matrix in cutaneous ageing: the effects of 0.1% copper-zinc malonate-containing cream on elastin biosynthesis," Exp Dermatol., 18(3):205-211.
Mcdevitt et al. (2003) "Spatially organized layers of cardiomyocytes on biodegradable polyurethane films for myocardial repair" Journal of Biomedical Materials Research A, 66:586-595.
Mithieux et al. (2004) "Synthetic elastin hydrogels derived from massive elastic assemblies of self-organized human protein monomers" Biomaterials, 25:4921-4927.

(56) References Cited

OTHER PUBLICATIONS

Mithieux et al. (2009) "In situ polymerization of tropoelastin in the absence of chemical crosslinking" Biomaterials, 30:431-435.

Mitts et al. (2010) "Aldosterone and mineralocorticoid receptor antagonists modulate elastin and collagen deposition in human skin," J. Invest Dermatol., 130(10):2396-2406.

Miyagawa et al. (2011) "Tissue-Engineered Cardiac Constructs for Cardiac Repair" Annals Thoracic Surgery, 91:320-329.

Moon and Kim (2006) "Preparation of Biodegradable Thermoresponsive Polyaspartamides with NIsopropylamine Pendent Groups (I)" Bull. Korean Chem. Soc. 27(12):1981-1984.

Nagapudi et al. (2002) "Photomediated Solid-State Cross-Linking of an Elastin-Mimetic Recombinant Protein Polymer" Macromolecules 35:1730-1737.

Nichol et al. (2010) "Cell-laden microengineered gelatin methacrylate hydrogels" Biomaterials, 31:5536-5544.

Okamoto et al. (1989) "Characteristics of Elastin Peptides in Coacervate States: Ph Effect and Possible Ion Transport Mechanism" Peptide Chemistry, $27^{th}$ ed. 369-374.

Ostresh et al. (1996) "Generation and Use of Nonsupport-Bound Peptide and Peptidomimetic Combinatorial Libraries" Methods in Enzymology, 267:220-234.

Ozturk et al. (2009) "Dynamic cell culturing and its application to micropatterned elastin-like protein-modified poly(N-isopropylacrylamide) scaffolds" Biomaterials 30:5417-5426.

Peppas et al. (2006) "Hydrogels in Biology and Medicine: From Molecular Principles to Bionanotechnology" Advanced Materials, 18:1345-1360.

Raphel et al. (2012) "Photoreactive elastin-like proteins for use as versatile bioactive materials and surface coatings†" Journal of Materials Chemistry, 22:19429-19437.

Rnjak et al. (2011) "Severe Burn Injuries and the Role of Elastin in the Design of Dermal Substitutes" Tissue Engineering, 17(2):81-91.

Rnjak-Kovacina et al. (2012) "Electrospun synthetic human elastin:collagen composite scaffolds for dermal tissue engineering" Acta Biomaterial, 8:3714-3722.

Sato et al. (2007) "Distinct steps of cross-linking, self-association, and maturation of tropoelastin are necessary for elastic fiber formation," J. Mol. Biol. 369(3):841-851.

Shifren et al. (2006) "The Stumbling Block in Lung Repair of Emphysema: Elastic Fiber Assembly," Proc Am Thorac Soc., 3:428-433.

Shimatake and Rosenberg (1981) "Purified a regulatory protein cII positively activates promoters for lysogenic development" Nature, 292:128-132.

Smith et al. (2010) "Duration of wrinkle correction following repeat treatment with Juvederm hyaluronic acid fillers" Arch. Dermatol Res. 302:757-762.

Sohm et al. (2011) "Evaluation of the efficacy of a dill extract in vitro and in vivo," Int J. Cosmet Sci. 33(2):157-163.

Sreerama et al. (2000) "Estimation of Protein Secondary Structure from Circular Dichroism Spectra: Comparison of CONTIN, SELCON, and CDSSTR Methods with an Expanded Reference Set" Analytical Biochemistry, 287:252-260.

Studier and Moffat (1986) "Use of Bacteriophage T7 RNA Polymerase to Direct Selective High-level Expression of Cloned Genes" J Mol. Biol. 189:113-130.

Sykes and Partridge (1974) "Salt Soluble Elastin from Lathyritic Chicks" Biochem. J. 141:567-572.

Tandon et al. (2009) "Electrical stimulation systems for cardiac tissue Engineering" Nature Protocols, 4(2):155-173.

Thompson et al. (1994) "CLUSTAL W: improving the sensitivity of progressive multiple sequence alignment through sequence weighting, position-specific gap penalties and weight matrix choice" Nucleic Acid Research, 22(22):4673-4680.

Vrhovski et al. (1997) "Coacervation characteristics of recombinant human tropoelastin" Eur. J. Biochem. 250:92-98.

Wagenseil (2007) "New insights into elastic fiber assembly," Birth Defects Res C Embryo Today, 81(4):229-240.

Ward and Georgiou (2011) "Thermoresponsive Polymers for Biomedical Applications" Polymers, 3:1215-1242.

Wise et al. (2009) "Engineered Tropoelastin and Elastin Based Biomaterials" Advances in Protein Chem. and Structural Biol. 78:1-24.

Wu et al. (1999) "Protein Chemistry and Structure: Glycosaminoglycans Mediate the Coacervation of Human Tropoelastin through Dominant Charge Interactions Involving Lysine Side Chains" J. of Biol. Chem. 274:21719-21724.

Yanagisawa and Davis (2010) "Unraveling the mechanism of elastic fiber assembly: The roles of short fibulins," Int. J. Biochem Cell Biol. 42(7):1084-1093.

Narins et al. (2008) "Persistence and Improvement of Nasolabial Fold Correction with Nonanimal-Stabilized Hyaluronic Acid 100,000 Gel Particles/mL Filler on Two Retreatment Schedules: Results up to 18 Months on Two Retreatment Schedules" Dermatological Surgery, 34:S2-S8.

Falcone & Berg (2008) "Crosslinked hyaluronic acid dermal fillers: a comparison of rheological properties" Journal of Biomedical Materials Research Part A, 87A:1:264-271.

Petite et al. (1994) "Use of diphenylphosphorylazide for cross-linking collagen-based biomaterials" Journal of Biomedical Materials Research Part A, 28:159-165.

Ai-Obeidi et al. (1998) "Peptide and Peptidomimetic Libraries," Mol Biotechnol; 9(3):205-223.

Altschul et al. (1990) "Basic Local Alignment Search Tool," J Mol Biol; 215(3):403-410.

Altschul et al. (1997) "Gapped BLAST and PSI-BLAST: a new generation of protein database search programs," Nucleic Acids Res; 25(17):3389-3402.

Anderson et al. (2004) "Nanoliter-scale synthesis of arrayed biomaterials and application to human embryonic stem cells," Nature Biotechnology; 22:863-866.

Anderson et al. (2005) "Biomaterial microarrays: rapid, microscale screening of polymer-cell interaction," Biomaterials; 26:4892-4897.

Dijke and Iwata (1989) "Growth Factors for Wound Healing," Bio Technology; 7:793-798.

Falsey et al. (2001) "Peptide and Small Molecule Microarray for High Throughput Cell Adhesion and Functional Assays," Bioconjugate Chemistry; 12:346-353.

Higgins et al. (1994) "CLUSTAL W: Improving the sensitivity of progressive multiple sequence alignment through sequence weighting, position-specific gap penalties and weight matrix choice," Nucleic Acids Res; 22(22):4673-4680.

Hruby et al. (1997) "Synthesis of oligopeptide and peptidomimetic libraries," Cuff Opin Chem Bio; 1:114-119.

Karlin and Altschul (1990) "Methods for assessing the statistical significance of molecular sequence features by using general scoring schemes," Proc Natl Acad Sci USA; 87(6):2264-2268.

Karlin and Altschul (1993) "Applications and statistics for multiple high-scoring segments in molecular sequences," Proc Natl Acad Sci USA; 90(12):5873-5877.

Li eat al. (2006) "Electrospinning polyaniline-contained gelatin nanofibers for tissue engineering applications," Biomaterials; 27(13):2705-2715.

Li et al. (2005) "Electrospun protein fibers as matrices for tissue engineering," Biomaterials; 26(30):5999-6008.

Liu et al (2001) "Nanostructured Materials Designed for Cell Binding and Transduction," Biomacromolecules; 2(2):362-368.

Miyamoto et al. (2009) "Creation of cross-linked electrospun isotypic-elastin fibers controlled cell-differentiation with new cross-linker," J Biol Macromolecules; 45:33-41.

Orner et al. (2004) "Arrays for the combinatorial exploration of cell adhesion," Journal of the American Chemical Society; 126:10808-10809.

Ostergaard and Holm (1997) "Peptomers: a versatile approach for the preparation of diverse combinatorial peptidomimetic bead libraries," Mol Divers; 3:17-27.

Taurniare et al. (2006) "Polymer microarrays for cellular adhesion," Chem Comm; 2118-2120.

(56) References Cited

OTHER PUBLICATIONS

Bobroff et al., Ten Year Experience with Use of Ilizarov Bone Transport for Tibial Defects, Bulletin (Hospital for Joint Diseases), 61-3&4, p. 101-107.
Giannoudis et al., Bone substitutes: An update, (2005) Injury, 36(3, Supplement), S20-S27.
Halm et al., Visualizing tropoelastin in a long-term human elastic fibre cell culture model, (2016) Scientific Reports 6.
Lavini et al., Bone transport and compression-distraction in the treatment of bone loss of the lower limbs, (2010) Injury 41 (11) p. 1191-1195.
Panagiotis, Classification of non-union, (2005) Injury, 36S:4 S30-S37.
Pape et al., Autologous Bone Graft: Properties and Techniques, (2010) Journal of Orthopaedic Trauma 24(Suppl 1): S36-40.
Pearson, Searching Protein Sequence Libraries: Comparison of the Sensitivity and Selectivity of the Smith-Waterman and FASTA Algorithms, (1991) Genomics 11:635-650.
Rnjak et al., Autologous Bone Graft: Properties and Techniques, (2009) Biomaterials 30.32: 6469-6477.
Rossetti et al., A novel anti-ageing mechanism for retinol: induction of dermal elastin synthesis and elastin fibre formation, (2011) International Journal of Cosmetic Science 33.1: 62-69.
Schindeler et al., Bone remodeling during fracture repair: The cellular picture, (2008) Seminars in Developmental Biology 19(5): p. 459-466.
Smith & Waterman, Identification of Common Molecular Subsequences, (1981) J. Mol. Biol. 147:195-197.
Wang et al., Tropoelastin Incorporation into a Dermal Regeneration Template Promotes Wound Angiogenesis, (2015) Advanced Healthcare Materials 4.4: 577-584.
Yamauchi et al., Fibulin-4 and -5, but not Fibulin-2, are Associated with Tropoelastin Deposition in Elastin-Producing Cell Culture, (2010) Acta Histochemica et Cytochemica 43.6:131-138.
Zeckey et al., The Aseptic Femoral and Tibial Shaft Non-Union in Healthy Patients—An Analysis of the Health-Related Quality of Life and the Socioeconomic Outcome, (2011) The Open Orthopaedics Journal 5:193-7.
Indik et al. (1990) "Production of Recombinant Human Tropoelastin: Characterization and Demonstration of Immunologic and Chemotactic Activity" Archives of Biochemistry and Biophysics, 280:80-86.

* cited by examiner

SCALABLE THREE-DIMENSIONAL ELASTIC CONSTRUCT MANUFACTURING

FIELD OF THE INVENTION

The invention relates to production of elastic materials from tropoelastin, and especially to the formation of materials into preferred three-dimensional shapes, and especially, although not exclusively, to materials that can be used for tissue therapy and repair.

BACKGROUND OF THE INVENTION

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

There is considerable, growing demand for three-dimensional constructs that can be used for human tissue repair. Constructs based on natural biomaterials (such as elastin) have emerged as leading candidates for various tissue engineering applications due to their remarkable properties including elasticity, self-assembly, long-term stability, and biological activity.

Tropoelastin is the substrate material for formation of elastin and elastic fibre. Elastin is formed from tropoelastin when tropoelastin is cross-linked.

Tropoelastin is soluble in most aqueous solutions, and indeed is soluble at physiological salt and pH. Tropoelastin can be induced to precipitate from an aqueous solution by heating an aqueous solution. The process is known as coacervation, in which tropoelastin monomers associate with each other by contact of hydrophobic regions of one tropoelastin monomer with the like regions of another monomer. This association of monomers is reversible, and the tropoelastin monomers in coacervated tropoelastin may be dissociated, for example by pH, salt or temperature modification, leading to dissolution of tropoelastin monomers of the coacervate into the solution and disappearance of the coacervate. What this means is that a coacervate of tropoelastin is not sufficiently robust to form a preferred three-dimensional elastic structure that is stable in physiological conditions.

The cross-linking of tropoelastin monomers, whether in coacervated form or otherwise, leads to a covalent bonding of tropoelastin monomers that ostensibly represents an association of tropoelastin monomers that cannot be dissociated by pH, salt or temperature adjustment. Generally, cross-linked tropoelastin monomers, as observed in elastin and elastic fibre, cannot be dissociated from each other unless the monomers are hydrolysed, as described in prior art processes for purification of elastin from natural sources.

Given the generally irreversible association of tropoelastin monomers observed in cross-linked tropoelastin as in elastin or elastic fibre, cross-linking of tropoelastin has been proposed as a solution to enable the formation of preferred three-dimensional elastic structures. Examples of this technology are disclosed in Miyamoto et al. (2009), WO 2008/033847 and WO 2009/099570 whereby electrospun material is cross-linked into preferred stable structures. Some of the cross-linking technologies require a heating step whereby a tropoelastin-containing composition is heated in the formation of a preferred elastic structure. Generally the heating step is required to evaporate solvent, and/or to provide the required temperature condition for the cross-linking reaction.

One problem with processes involving cross-linking is that the cross-linking agents are not biocompatible in the context of either tolerance of tissue to the chemistry of cross-linkers, nor residual unreacted cross-linker, nor to elastic function of the cross-linked material. Another problem is that it is difficult to form a preferred structure from cross-linked material, because after cross-linking, a material quickly solidifies into a type of structure which cannot then be conformed to a preferred robust shape. Therefore there are limitations as to the extent to which such processes can be used in forming structures by spraying moulding technologies and the like.

Ultimately, what is required to form a stable preferred three-dimensional structure from tropoelastin monomers is to link the monomers with each other in such a way so as to prevent a dissociation from one another that would result in loss of the preferred structure or shape. Another approach to forming a stable elastic three-dimensional construct is to use other molecules, which ostensibly act as linkers for linking one tropoelastin monomer with another. Examples include synthetic polymers generally as discussed in WO 2009/099570. Another approach is to spray or coat a water insoluble substrate with a solution of soluble elastic monomers as in WO 2012/080706, WO 2011/127478 and WO 2007/029913. In this latter approach, the insoluble substrate, such as a nano-fibrous web, as in WO 2007/029913, or a tube, as in WO 2011/127478 ostensibly links the tropoelastin monomers to each other so that they do not dissociate in aqueous conditions. The problem with these approaches is that inevitably it is the insoluble substrate that provides the preferred three-dimensional shape, not the molecular components, which impacts on the overall elastic profile of the structure and limits the ability to build three-dimensional structures.

There is a need for new approaches to the formation of elastic three-dimensional structures.

SUMMARY OF THE INVENTION

The invention seeks to address, or at least to provide an improvement to, one or more of the above mentioned limitations, needs or problems and in one embodiment provides a method for forming an elastic material, including:
 providing a solution of tropoelastin monomers;
 applying the solution to a surface;
 heating the solution on the surface to a temperature sufficient to enable the tropoelastin monomers to bind to each other to form an elastic material that does not dissociate into tropoelastin monomers when the material is contacted with an aqueous solution,
thereby forming the elastic material.

In another embodiment there is provided a method for forming an elastic material including:
 providing a solution of tropoelastin monomers;
 applying the solution to a surface;
 heating the solution on the surface to a temperature within a range defined by a minimum value and a maximum value;
  wherein the minimum value is a temperature above which tropoelastin monomers are bonded to each other to form a material that does not dissociate in an aqueous solution; and
  wherein the maximum value is a temperature above which a non-elastic material is formed;

thereby forming an elastic material.

In another embodiment there is provided an elastic material formed by a method described above.

In another embodiment there is provided a method for forming an elastic hydrogel, including:
   forming an elastic material according to a method described above;
   contacting the elastic material with an aqueous solution.

In another embodiment there is provided an elastic hydrogel formed by a method described above.

In another embodiment there is provided a construct, implant or device including an elastic material or hydrogel described above.

In other embodiments there are provided methods and uses of the elastic material, hydrogel, device, implant or construct described above for repairing and/or restoring biological tissue, and for use of the elastic material in assay applications.

The present invention will now be more fully described with reference to the accompanying examples and drawings. It should be understood, however, that the description following is illustrative only and should not be taken in any way as a restriction on the generality of the invention described above.

DETAILED DESCRIPTION OF THE EMBODIMENTS

Figure 1:
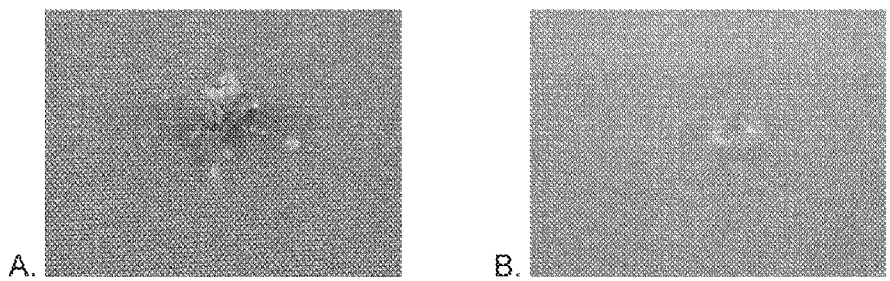
FIG. 1. Heat-treated water-based tropoelastin solution A. After heating to 160° C. B. After wetting in PBS.
Figure 2:
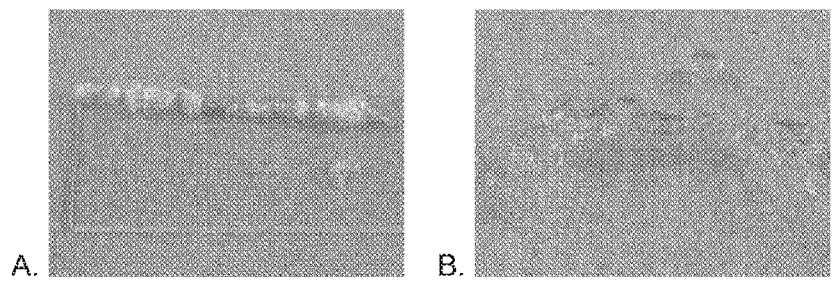
FIG. 2. Heat-treated HFP-based tropoelastin solution A. After heating to 160° C. B. After wetting in PBS.
Figure 3:
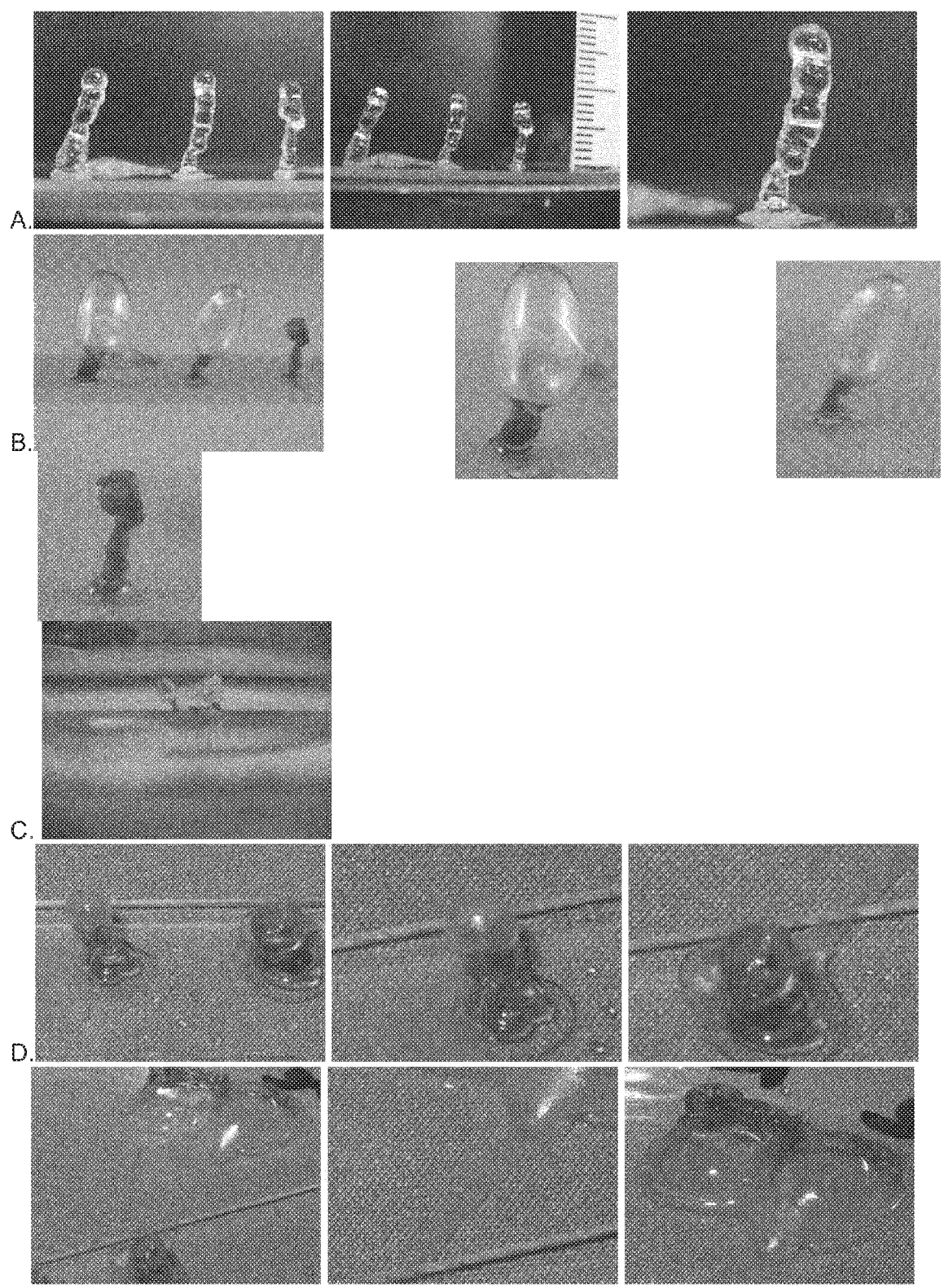
FIG. 3. Heat-treated 70% ethanol-based tropoelastin solution A. Before heating to 160° C. B. After heating to 160° C. C. Side on view in PBS. D. After wetting in PBS.
Figure 4:
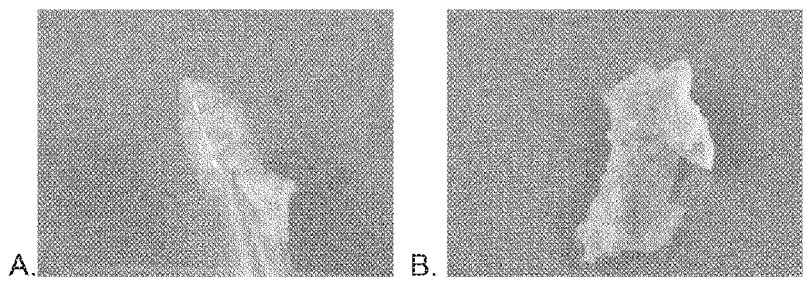
FIG. 4. Heat-treated HFP-based tropoelastin solution used to coat tubing. A. After heating to 160° C. B. After wetting in PBS.
Figure 5:
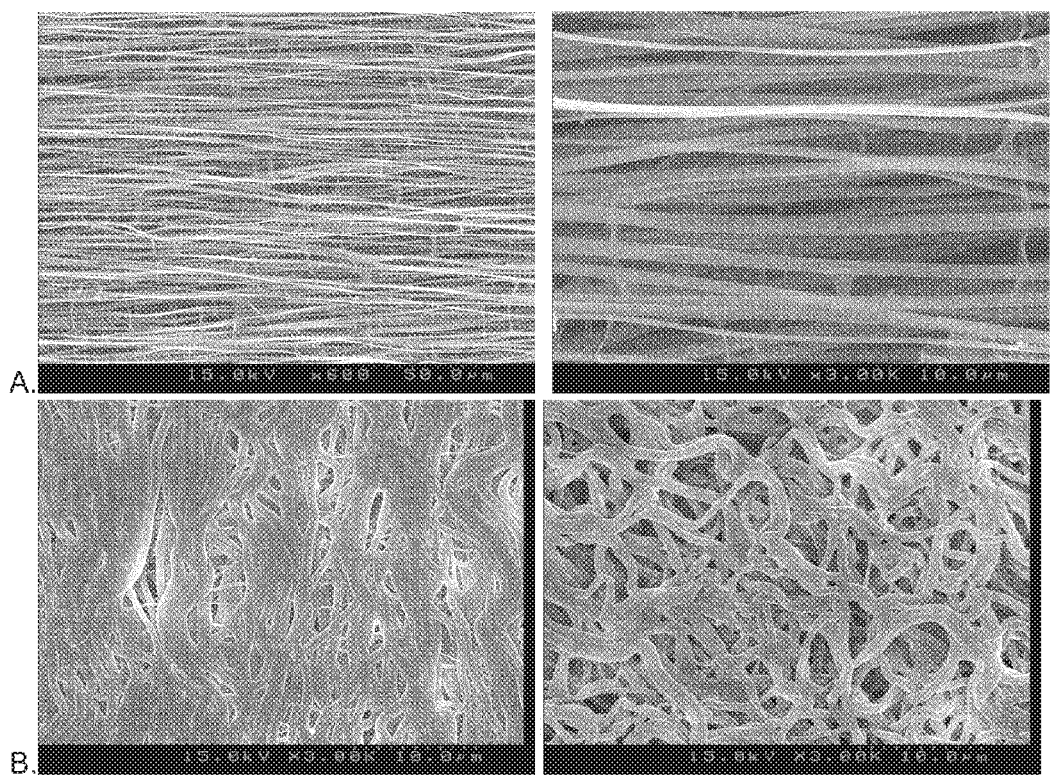
FIG. 5. Scanning electron microscopy images of heat-treated electrospun tropoelastin. A. After heating to 160° C. B. After wetting in PBS.
Figure 6:
FIG. 6. Scanning electron microscopy image of fibroblasts cultured on heat-treated electrospun tropoelastin.
Figure 7:
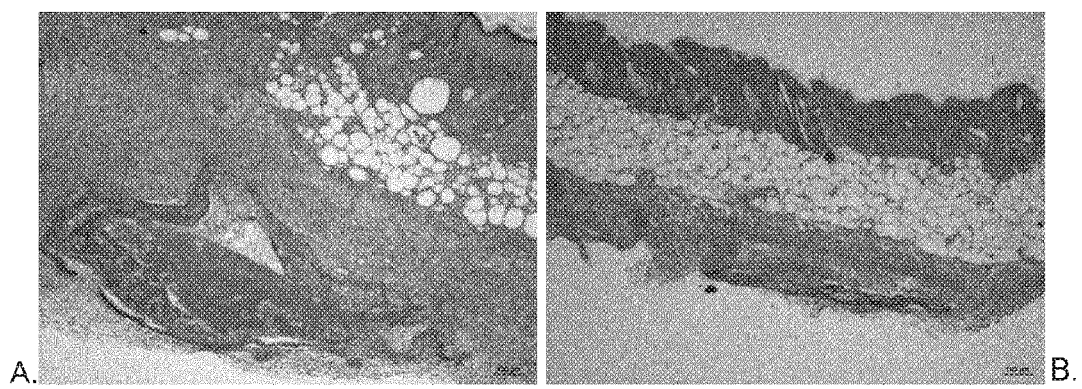
FIG. 7. Images of WG stained skin biopsies showing persistence of heat-treated electrospun tropoelastin.
Figure 8:
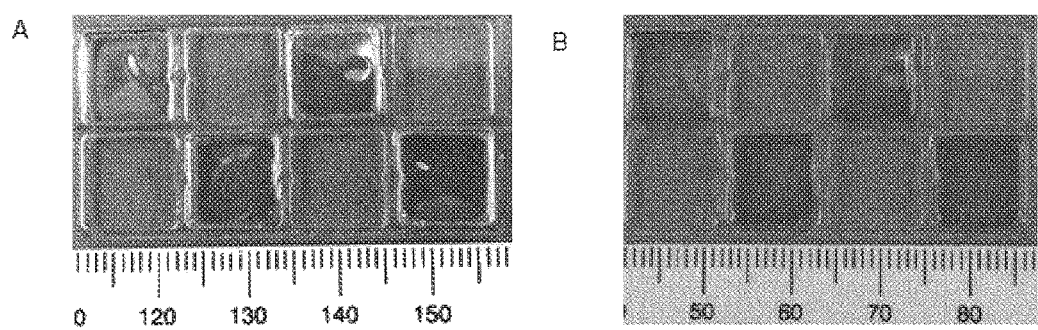
FIG. 8. Films made from a heat-treated water-based tropoelastin solution A) after drying at 37° C. for 16 h B) after further heating to 160° C. for 4 h.
Figure 9:
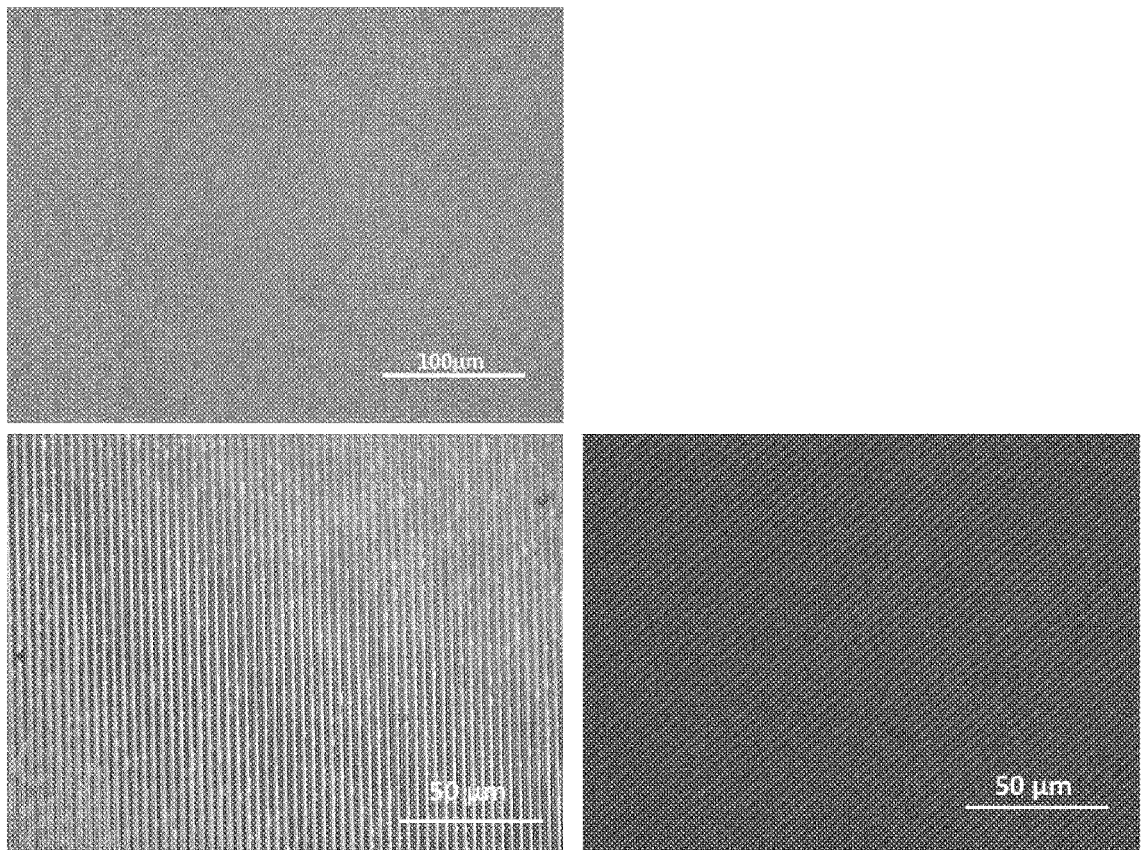
FIG. 9. Micropatterned films made from a heat-treated water-based tropoelastin solution. Groove patterns are 500 nm deep and 3.5 μm wide.
Figure 10:
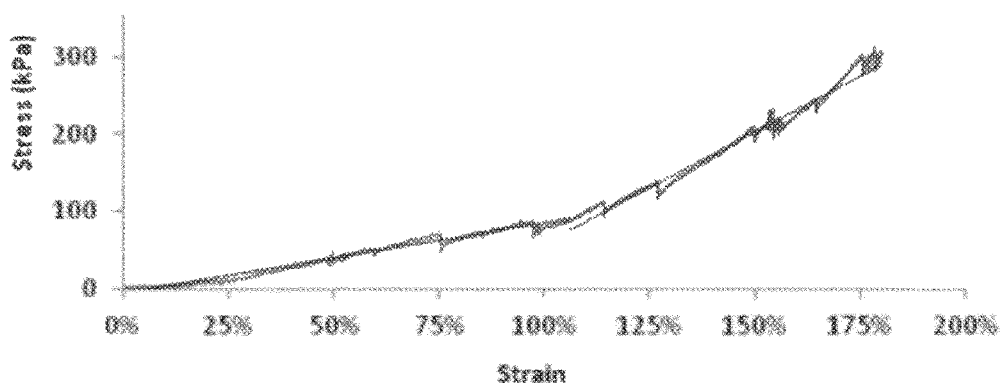
FIG. 10. Calculation of moduli at 0-105% and 105-19% extension.

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

A person skilled in the art will recognize many methods and materials similar or equivalent to those described herein, which could be used in the practice of the present invention. The present invention is in no way limited to the methods and materials described.

It will be understood that the invention disclosed and defined in this specification extends to all alternative combinations of two or more of the individual features mentioned or evident from the text or drawings. All of these different combinations constitute various alternative aspects of the invention.

All of the patents and publications referred to herein are incorporated by reference in their entirety.

The present work demonstrates, for the first time, that a biocompatible material having desirable properties such as strength and elasticity can be synthesized by a simple process through heating tropoelastin. Accordingly, the present invention provides a reliable, scalable, inexpensive path to manufacturing biocompatible three-dimensional elastic materials. The invention is amenable to high throughput production and uses protein to produce a versatile range of biomaterials (such as sheets, tubes and fibres) that are useful in therapeutic and in vitro assay applications. The materials produced by the process of the present invention possess the properties of elasticity and strength that are the hallmarks of native elastin but are devoid of chemical contaminants and toxic by-products that are commonly found in, or associated with, constructs formed from the use of cross-linking agents.

The advantageous properties of the materials of the present invention are discussed throughout the present specification, and in particular, are exhibited in the Examples, which show that the materials of the present invention can be made in a simple manner by heating of a solution of tropoelastin, and that the materials formed possess the required properties of biocompatibility, strength, resilience, cell binding and extracellular matrix interactions that enable them to be used in tissue engineering applications, as well as in the construction of in vitro assays.

As mentioned above, scaffolds based on biomaterials have been used for tissue engineering applications because of their biocompatibility and mechanical properties. However, prior art methods of synthesising three-dimensional biomaterial-based constructs are inefficient, slow and restricted, and the alternative, traditional tissue engineering technologies overwhelmingly require the use of slow and expensive methods (which can take weeks to produce a construct), are generally diffusion-constrained to several hundred microns thickness, and are regularly burdened by toxicity component or by-product issues that demand regulatory compliance.

Thus in one embodiment there is provided a method for forming an elastic material, including:
   providing an aqueous solution of tropoelastin monomers;
   applying the solution to a surface;
   heating the solution on the surface to a temperature sufficient to enable the tropoelastin monomers to bind to each other to form an elastic material that does not dissociate into tropoelastin monomers when the material is contacted with an aqueous solution,
thereby forming the elastic material.

An important finding of the invention is that the heating step enables the association of the tropoelastin monomers with such affinity that the monomers do not substantially dissociate when the aggregate is contacted with an aqueous solution. The heating forms an elastic aggregate, mass or material that is different to a coacervate to the extent that it does not dissociate into individual monomers in physiological conditions, and different to elastic fibre or other material in the sense that it does not require cross-linking of monomers with toxic cross-linking agents such as glutaraldehyde, or use of a solvent having a basic pH, to maintain itself in a solid phase, or to retain the permanency of the shape in which it is formed. The advantage is that the process more or less permanently assembles biocompatible monomers into a permanent structure or shape that can be used in tissue applications without toxicity concerns.

Typically the solution is heated to a temperature that is sufficient to enable the tropoelastin monomers to bind to each other to form an elastic material that does not dissociate into tropoelastin monomers when the material is exposed to physiological conditions, especially human physiological conditions. In particular, the aggregate does not dissociate under physiological conditions of temperature and pH. Advantageously, the aggregate does not dissociate under the following conditions of:

temperature (from about 30 to about 45° C.);
salt (concentration of about 75 mM to about 300 mM);
pH (of about 6.5 to about 8.0).

Therefore, this material is suitable for use not only under physiological conditions, but also in other applications, such as in vitro assays, where it may be exposed to other, more demanding conditions. Notably, this material is achieved without having to perform any cross-linking of the tropoelastin monomers and without using a scaffold to bind assemblies of the peptide thereto.

The material formed by the process of the present invention has a number of advantages. Firstly, the tropoelastin monomers remain bound with each other so that the three-dimensional shape of the elastic material formed from the aggregate is retained in an aqueous environment. Secondly, the properties of the starting material that make tropoelastin so useful in tissue engineering applications (for example, elasticity, strength, resilience, and biocompatibility) are retained in the end-product. Thirdly, while the aggregate may take up water in an aqueous solution to form a hydrogel, in doing so the aggregate does not dissociate, thereby maintaining the three-dimensional structure of the elastic material.

In one embodiment the solution is heated to a temperature that is sufficient to enable the tropoelastin monomers to bind to each other to form an elastic material that does not dissociate into tropoelastin monomers when the material is contacted with an aqueous solution having a pH of from about 6.5 to about 8.0. As used herein a wording defining the limits of a range of length such as, for example, "from 1 to 5" means any integer from 1 to 5, i.e. 1, 2, 3, 4 and 5. In other words, any range defined by two integers explicitly mentioned is meant to include and disclose any integer defining said limits and any integer included in said range. For example, the solution may have a pH of about 6.6, about 6.7, about 6.8, about 6.9, about 7.0, about 7.1, about 7.2, about 7.3, about 7.4, about 7.5, about 7.6, about 7.7, about 7.8, about 7.9, or about 8.0.

In one embodiment the solution is heated to a temperature that is sufficient to enable the tropoelastin monomers to bind to each other to form an elastic material that does not dissociate into tropoelastin monomers when the material is contacted with an aqueous solution having a temperature of from about 30 to about 45° C. For example, the temperature may be about 31° C., about 32° C., about 33° C., about 34° C., about 35° C., about 36° C., about 37° C., about 38° C., about 39° C., about 40° C., about 41° C., about 42° C., about 43° C., about 44° C., or about 45° C.

In one embodiment the solution is heated to a temperature that is sufficient to enable the tropoelastin monomers to bind to each other to form an elastic material that does not dissociate into tropoelastin monomers when the material is contacted with an aqueous solution having a salt concentration of about 75 mM to about 300 mM. For example, the salt concentration may be about 75 mM, about 80 mM, about 85 mM, about 90 mM, about 95 Mm, about 100 mM, about 110 mM, about 120 mM, about 130 mM, about 140 mM, about 150 mM, about 160 mM, about 170 mM, about 180 mM, about 190 mM, about 200 mM, about 210 mM, about 220 mM, about 230 mM, about 240 mM, about 250 mM, about 260 mM, about 270 mM, about 280 mM, about 290 mM, or about 300 mM.

In one embodiment, the solution is heated to a temperature that is sufficient to enable the tropoelastin monomers to bind to each other to form an elastic material that does not dissociate into tropoelastin monomers when the material is exposed to physiological conditions (e.g. pH of between about 7.2 and about 7.5, a temperature of between about 36 and about 37° C., and a salt concentration of about 150 mM).

In accordance with the process, the solution is heated to form the elastic material of the present invention. As discussed above, the purpose of the heating step is to form a material containing associated tropoelastin monomers, more specifically, to enable the tropoelastin monomers to bind to each other to form an elastic material that does not then dissociate into tropoelastin monomers when the elastic material is contacted with aqueous solution. The heating step is to be carried out at a temperature sufficient to enable the tropoelastin monomers in the concentrate to bind to each other to form an aggregate or material including tropoelastin monomers. Typically, heating will be carried out at a temperature of about 100° C. or greater, for example from 100° C. to 160° C. For example, the temperature of the heating step may be 110° C. or greater, 120° C. or greater, 130° C. or greater, 140° C. or greater, 150° C. or greater, 160° C. or greater, 170° C. or greater, or 180° C. or greater. Preferably, the temperature is between about 120° C. and about 180° C., between about 130° C. and about 170° C., or between about 140° C. and about 160° C. Most preferably, the temperature is about 160° C.

In another embodiment there is provided a method for forming an elastic material including:
  providing a solution of tropoelastin monomers;
  applying the solution to a surface;
  heating the solution on the surface to a temperature within
    a range defined by a minimum value and a maximum
    value;
    wherein the minimum value is a temperature above
      which tropoelastin monomers are bonded to each
      other to form a material that does not dissociate in an
      aqueous solution; and
    wherein the maximum value is a temperature above
      which a non-elastic material is formed.

According to the embodiment, below the minimum value, the elastic material of the invention is not formed. That is to say that what is formed is dissociable in aqueous solution, particularly in physiological conditions. Therefore, below the minimum value, something more resembling a coacervate may be formed. Below the maximum value, the material retains the elastic properties discussed herein. Above the maximum value, the material may lose properties of elasticity.

Suitable lengths of time over which the heating of the solution should be carried out include about 10 minutes or more, about 20 minutes or more, about 30 minutes or more, about 40 minutes or more, about 50 minutes or more, about 1 hour or more, about 2 hours or more, about 3 hours or more, about 4 hours or more, or about 5 hours or more.

However, a person skilled in the art will understand that the temperature to which the solution should be heated as well as the time over which the solution should be heated will vary depending on various factors, such as:
- the type of heating method employed (for example, dry heating, flash heating, etc);
- the concentration of the tropoelastin monomers in the solution;
- the volume of solution;
- the composition of the tropoelastin monomers;
- the degree of association desired in the aggregate or elastic material;
- the relative humidity during heating.

In certain embodiments, heating from 8 to 16 hours may be used to provide a substance which is more crystalline and yet retains elastic properties.

Generally the humidity during heating may be from about 20 to about 80%, preferably about 35, 45, 55, 65 or 75% relative humidity.

As described herein, the heating step may result in the formation of an elastic material that develops a colour change. Thus, in certain embodiments, one may test for the formation of an elastic material, or to check for completion of the heating step, by determining whether the material has developed a colour change. A colour change is generally a change from the normal translucent appearance of elastin to a colour which may be yellow or brownish. It is not necessary that the whole of the material develops a colour change. Generally the colour change may be reduced in the elastic material by hydration.

A person skilled in the art will also be aware that, by utilising different heating methods, aggregates with different internal structures can be obtained. For example, flash-heating would involve subjecting the concentrate to an intense source of heat for only a very limited amount of time. Accordingly, heating will occur for a sufficient amount of time to associate the monomers to form the aggregate, but will be too fast for all solvent trapped in the aggregate to evaporate from the aggregate, thereby forming an aggregate having a vacuole-type structure. Further, the aggregate could be heated again such that the trapped solvent evaporates, thereby forcing the vacuoles to expand, and resulting in the formation of a porous aggregate. A person skilled in the art will also be aware that solvent may not be present internally in the aggregate, but may be present on the external surface of the aggregate (in addition to or as an alternative to the solvent present inside the aggregate).

One particularly important advantage of the process is that in certain embodiments the material formed by the process may be ostensibly gas impermeable, resulting from a close alignment of protein molecules, which is retained by the heating step. This enables the material to be blown into a particular shape, much the same as occurs in glass blowing techniques.

Regardless of which heating method is used, a person skilled in the art will understand that the aggregate formed by heating of the solution may therefore include water, to varying degrees. For example, the aggregate may include a significant amount of water (for example, more than about 60% w/w water), making it essentially a hydrogel. Alternatively, water may be present in the aggregate in an amount of only about 10% w/w. Because water content influences elasticity, the elasticity of the aggregate (and therefore the material) can be varied by varying the water content of the aggregate, which, in turn, can be varied by changing various factors such as the amount of water present in the concentrate prior to heating, as well as the heating time, method and temperature.

In one embodiment, the elastic material has a solvent content of from greater than about 0 to about 50% (w/w) of the material at the completion of the heating step. For example, the elastic material may have a solvent content of from about 0.5% (w/w), about 1% (w/w), about 2% (w/w), about 3% (w/w), about 4% (w/w), about 5% (w/w) about 10% (w/w), about 15% (w/w), about 20% (w/w), about 25% (w/w), about 30% (w/w), about 35% (w/w), about 40% (w/w), about 45% (w/w), or about 50% (w/w). In one embodiment, the solvent is water.

The solution may be heated by directly heating the solution, or by heating the surface onto which the solution is placed. In the latter embodiment, the surface may be heated before the solution is applied to it, or it may be at room temperature at the time of application of the solution and then heated to the relevant temperature. Therefore, in one embodiment, the surface is heated for heating of the solution.

As also discussed above, a major advantage of the process of the present invention is that biocompatible materials can be formed because the process does not require the use of agents such as cross-linkers to effect the polymer formation. Accordingly, in one embodiment, the process of the present invention excludes the use of cross-linking agents.

In another embodiment, the process may exclude the use of salts, or other coacervation agents, to assist in the formation of tropoelastin-based polymers.

In another embodiment, the process may exclude the use of pH-modifying agents that effect irreversible aggregation of the tropoelastin monomers. In particular, in one embodiment the heating step is carried out at a pH that is not an alkaline pH, for example, the pH may be generally less than 8.5 or 8.0.

As discussed above, the materials of the present invention are formed by heating a solution of tropoelastin on a surface (such as, for example, in a shaped mold). Without wishing to be bound by any theory or mode of action, the present inventors believe that in a concentrated solution of tropoelastin, the tropoelastin monomers are closely packed. This close-packing facilitates bonding between the monomers upon heating of the solution, thereby producing an elastic material that does not dissociate into separate tropoelastin monomers when put in an aqueous environment.

The solution forming the solvent of the tropoelastin monomers may be an aqueous solution or a non-aqueous solution.

As used herein, the term "aqueous solution" refers to a water-containing solution. An aqueous solution may include other components, such as buffers, and pharmaceutically-acceptable excipients, and may also include other organic, water-miscible solvents, such as methanol, ethanol and hexafluoropropanol, and combinations thereof. Where the aqueous solution includes other solvents, a person skilled in the art will understand that water will be the major solvent component and the other solvent(s) will make up the minor portion of the solvent component. The use of an aqueous solution is particularly advantageous because it means that the tropoelastin concentrate, and therefore the material, is formed from a composition that does not contain any components that are non-biocompatible or toxic, or that may degrade in the body to form toxic or undesirable by-products. Accordingly, preferably, the aqueous solution does not contain any components (solvents, buffers, etc) that are toxic or non-biocompatible and/or that form toxic or non-biocompatible species when the material is in use (for example, in the body or in an assay).

As used herein, the term "non-aqueous solution" refers to a solution that either does not contain water, or that contains water as a minor solvent component. Examples of non-aqueous solvents include HFP, for example, as exemplified in the examples here. One advantage of using a non-aqueous solvent to form a non-aqueous solution is that generally the solvent may have a lower boiling point than water. This would enable the solvent to be evaporated as required during the process without the substantial addition of heat.

In one embodiment, the solution is formed by a process including the steps of:
providing a solution of tropoelastin monomers;
increasing the concentration of tropoelastin monomers in the solution.

The end product may be referred to as a "concentrate". The concentrate may be obtained, by any method known to be suitable to a person skilled in the art. It is believed that in the concentrate, tropoelastin monomers are brought into close contact with each other, such that, upon heating, the monomers will form an aggregate or mass, which can conform to the shape of the surface on which it is formed, and which does not dissociate or experience significant disruption of the linkages formed during heating when the aggregate is placed in an aqueous environment.

The concentrate may be obtained by evaporating the solvent from the solution by, for example, heating the solution, or blowing air or nitrogen over the solution. Thus, in one embodiment, the concentration of tropoelastin monomers is increased by evaporating solvent from the solution.

The solvent may be evaporated from the solution when the solution is applied to the surface. The solvent may be evaporated enabling concentration of the tropoelastin monomers as the solution is heated on the surface to a temperature enabling the tropoelastin monomers to bind to each other to form an elastic material that does not dissociate into tropoelastin monomers when the material is contacted with an aqueous solution.

In one embodiment, the concentration of tropoelastin monomers is increased by separating tropoelastin monomers from solvent. The tropoelastin monomers may be separated from the solvent by electrospinning of the tropoelastin monomers. "Electrospinning" is a process in which fibers are formed from a solution or melt by streaming an electrically charged solution or melt through a hole across a potential gradient. In one embodiment, the solution has a concentration of tropoelastin monomers from about 1% to about 40% (w/v) at the time that the solution is applied to the surface. For example, the concentration of tropoelastin monomers in the solution may be about 2%, about 3%, about 4%, about 5%, about 6%, about 7%, about 8%, about 9%, about 10%, about 12%, about 14%, about 16%, about 18%, about 20%, about 22%, about 24%, about 26%, about 28%, about 30%, about 32%, about 34%, about 36%, about 38%, or about 40% (w/v).

"Electrospun material" is any molecule or substance that forms a structure or group of structures (such as fibers, webs, or droplets), as a result of the electrospinning process. Generally, this material may be natural, synthetic, or a combination of these but in the present invention it is preferred that tropoelastin is used.

The matrix material may be deposited on the textile template using electrospinning. This platform technology is widely used in tissue engineering to fabricate scaffolds composed of nano- and micro-fibrous architecture (Li et al. (2006) and Li et al. (2005)).

The process of electrospinning involves placing a polymer or monomer-containing fluid (for example, a polymer or monomer solution, polymer or monomer suspension, or polymer or monomer melt) in a reservoir equipped with a small orifice, such as a needle or pipette tip, and a metering pump. One electrode of a high voltage source is placed in electrical contact with the fluid or orifice, while the other electrode is placed in electrical contact with a target (typically a collector screen or rotating mandrel). During electrospinning, the fluid is charged by the application of high voltage to the solution or orifice (for example, about 3 to about 15 kV) and then forced through the small orifice by the metering pump, providing a steady flow. While the fluid at the orifice normally would have a hemispherical shape due to surface tension, the application of the high voltage causes the otherwise hemispherically-shaped fluid at the orifice to elongate to form a conical shape known as a Taylor cone. With sufficiently high voltage applied to the fluid and/or orifice, the repulsive electrostatic force of the charged fluid overcomes the surface tension and a charged jet of fluid is ejected from the tip of the Taylor cone and accelerated towards the target, which typically is biased between −2 to −10 kV. A focusing ring with an applied bias (for example, 1 to 10 kV) may be optionally used to direct the trajectory of the charged jet of fluid. As the charged jet of fluid travels towards the biased target, it undergoes a complicated whipping and bending motion. If the fluid is a monomer or polymer solution or suspension, the solvent typically evaporates during mid-flight, leaving behind a polymer or monomer fiber on the biased target. If the fluid is a polymer or monomer melt, the molten monomer/polymer cools and solidifies in mid-flight and is collected as a monomer/polymer fiber on the biased target. As the polymer/monomer fibers accumulate on the biased target, a porous mesh is formed on the biased target.

The properties of the electrospun matrix may be tailored by varying the electrospinning conditions. For example, when the template is relatively close to the orifice, the resulting electrospun mesh tends to contain unevenly thick fibers, such that some areas of the fiber have a "bead-like" appearance. However, as the template is moved further away from the orifice, the fibers of the mesh tend to be more uniform in thickness. Moreover, the template may be moved relative to the orifice. In certain embodiments, the template is moved back and forth in a regular and periodic fashion, such that fibers of the mesh are substantially parallel to each other. When this is the case, the resulting mesh may have a higher resistance to strain in the direction parallel to the fibers, compared to the direction perpendicular to the fibers. In other embodiments, the biased target is moved relative to the orifice in a two- or three-dimensional pattern to create a mesh comprising one or more patterned layers with similar or different strand orientation, thickness, etc. In other embodiments, the template is moved randomly relative to the orifice, so that the resistance to strain in the plane of the mesh is isotropic. The properties of the electrospun matrix may also be varied by changing the magnitude of the voltages applied to the electrospinning system. In a non-limiting example, the electrospinning apparatus includes an orifice biased to 20 kV. In another non-limiting example, the electrospinning apparatus includes a template biased to −7 kV. In yet another non-limiting example, the electrospinning apparatus includes a focusing ring biased to 3 kV.

In one embodiment, the concentration of tropoelastin in the solution is between about 10 and about 350 mg/mL at the time that the solution is applied to the surface. For example, the concentration of tropoelastin is about 15 mg/mL, about 20 mg/mL, about 25 mg/mL, about 30 mg/mL, about 35 mg/mL, 40 mg/mL, about 45 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL, about 100 mg/mL, about 110 mg/mL, about 120 mg/mL, about 130 mg/mL, about 140 mg/mL, about 150 mg/mL, about 160 mg/mL, about 170 mg/mL, about 180 mg/mL, about 190 mg/mL, about 200 mg/mL, about 210 mg/mL, about 220 mg/mL, about 230 mg/mL, about 240 mg/mL, about 250 mg/mL, about 260 mg/mL, about 270 mg/mL, about 280 mg/mL, about 290 mg/mL, about 300 mg/mL, about 310 mg/mL, about 320 mg/mL, or about 340 mg/mL.

In one embodiment, the concentration of tropoelastin in the solution may depend on the type of solvent and the temperature of the solvent at which the tropoelastin is added to it.

The solution or concentrate of tropoelastin that is applied to the surface may have a range of viscosities. It may include precipitated non-cross linked tropoelastin, such as a coacervate.

In a certain embodiment, the solution applied to the surface may also include coacervated tropoelastin monomers.

In one embodiment there is provided a method for forming an elastic material, including:
providing a solution of tropoelastin monomers;
increasing the concentration of tropoelastin monomers in the solution to form a concentrate of tropoelastin;
applying the concentrate to a surface;
heating the concentrate on the surface to a temperature sufficient to enable tropoelastin in the concentrate to bind to each other to form an elastic material that does not dissociate into tropoelastin monomers when the material is contacted with an aqueous solution,
thereby forming the elastic material. In one embodiment, the concentrate is heated to a temperature within a range defined by a minimum value and a maximum value;
wherein the minimum value is a temperature above which tropoelastin monomers are bonded to each other to form a material that does not dissociate in an aqueous solution; and
wherein the maximum value is a temperature above which a non-elastic material is formed;
thereby forming an elastic material. The method may involve the step of heating the concentrate on the surface to enable a water loss of from about 1 to 20% water (w/w), preferably about 15% water (w/w) of the concentrate.

Tropoelastin is a monomeric protein encoded by the elastin (ELN) genomic sequence (or gene). Tropoelastin monomers are approximately 60-70 kDa in size. There are about 36 small domains in tropoelastin and each weighs about 2 kDa. Within the exons, there are alternating hydrophobic domains rich in non-polar amino acids such as glycine, valine, proline, isoleucine and leucine (which domains often occur in repeats of three to six peptides such as GVGVP, GGVP and GVGVAP), and hydrophilic domains rich in lysine and alanine. The hydrophilic domains often consist of stretches of lysine separated by two or three alanine residues such as AAAKAAKAA. Additionally, tropoelastin ends with a hydrophilic carboxy-terminal sequence containing its only two cysteine residues. Tropoelastin does not undergo cleavage during assembly and forming the microfibril is achieved by a self-association process termed coacervation.

Tropoelastin aggregates at physiological temperature due to interactions between hydrophobic domains. This process is reversible and thermodynamically controlled. The coacervate is stabilized by cross-linking via lysyl oxidase. The coacervate then becomes insoluble and the process is irreversible. It then condenses to form a cross-linked structure of two residues or four residues in either desmosine or isodesmosine.

In certain embodiments the tropoelastin monomer that is used in the present invention includes both hydrophilic and hydrophobic domains. Hydrophilic domains contribute to elastic function (by, for example, binding to water). They also contribute to a wider variety of biological functions including binding to cells and to the extra-cellular matrix. The hydrophobic domains are believed to be important for providing the elasticity that is a feature of the materials of the present invention.

Some examples of amino acid sequences that may be present in a tropoelastin monomer are as follows:

```
GGVPGAIPGGVPGGVFYP

GVGLPGVYP

GVPLGYP

PYTTGKLPYGYGP

GGVAGAAGKAGYP

TYGVGAGGFP

KPLKP

ADAAAAYKAAKA

GAGVKPGKV

GAGVKPGKV

TGAGVKPKA

QIKAPKL

VAPGVG

VPGVG

AAAAAAAKAAAK

AAAAAAAAAKAAKYGAAAGLV

EAAAKAAAKAAKYGAR

EAQAAAAAKAAKYGVGT

AAAAAKAAAKAAQFGLV

GGVAAAAKSAAKVAAKAQLRAAAGLGAGI

GALAAAKAAKYGAAV

AAAAAAAKAAAKAA

AAAAKAAKYGAA

CLGKACGRKRK.
```

The tropoelastin for use in the present invention may, in certain embodiments, include or consist of, any one of the above described sequences.

In one embodiment the tropoelastin for use in the present invention includes or consists of a sequence shown below:

VXPGVG where X is any amino acid residue or no residue

ZXPGZG wherein Z is an aliphatic residue

VXP(I/L/V)V(I/L/V)

wherein (I/L/V) is isoleucine, leucine or valine.

In one embodiment, the tropoelastin monomers contain hydrophilic and hydrophobic domains of tropoelastin.

Other suitable tropoelastin sequences are known in the art and include CAA33627 (*Homo sapiens*), P15502 (*Homo sapiens*), AAA42271 (*Rattus norvegicus*), AAA42272 (*Rattus norvegicus*), AAA42268 (*Rattus norvegicus*), AAA42269 (*Rattus norvegicus*), AAA80155 (*Mus musculus*), AAA49082 (*Gallus gallus*), P04985 (*Bos taurus*), ABF82224 (*Danio rerio*), ABF82222 (*Xenopus tropicalis*) and P11547 (*Ovis aries*). In a preferred embodiment, the tropoelastin monomers for use in the present invention are derived from human tropoelastin. In one embodiment, they have the sequence corresponding to amino acid residues 27-724 of GenBank entry AAC98394. As stated herein, the present invention also includes variants, for example species variants or polymorphic variants, of tropoelastin.

The tropoelastin monomers for use in the present invention may be obtained from recombinant sources. They can also be extracted from natural sources or synthesised (by, for example, solid-phase synthesis techniques). Tropoelastin monomers are also commercially available.

There are a number of isoforms of tropoelastin and therefore the exact number of amino acids that make up the tropoelastin polypeptide will vary. The term "polypeptide" or "polypeptide chain" refers to a polymer of amino acids, usually linked together by amide bonds. A functionally-active polymer of amino acids is generally referred to as a "protein". The present invention also includes variants of tropoelastin, for example species variants or polymorphic variants. The present invention is intended to cover all functionally-active variants of tropoelastin that exhibit the same activity (i.e. biocompatibility and elasticity). This also includes apo- and holo-forms of tropoelastin, post-translationally modified forms, as well as glycosylated or de-glycosylated derivatives. Such functionally-active fragments and variants include, for example, those having conservative amino acid substitutions.

In one embodiment, the monomers are recombinant tropoelastin monomers having the sequence of a human tropoelastin isoform.

The term "functionally-active" in relation to a fragment or variant of tropoelastin means the fragment or variant (such as an analogue, derivative or mutant) that is capable of forming an elastic material, as discussed further below. Such variants include naturally-occurring variants and non-naturally occurring variants. Additions, deletions, substitutions and derivatizations of one or more of the amino acids are contemplated so long as the modifications do not result in loss of functional activity of the fragment or variant. A functionally-active fragment can be easily determined by shortening the amino acid sequence, for example using an exopeptidase, or by synthesizing amino acid sequences of shorter length, and then testing for elastic material formation ability such as by the methods illustrated in the examples below.

Where non-natural variations occur, the fragment may be called a peptidomimetic, which are also within the scope of the invention. For example, synthetic amino acids and their analogues may be substituted for one or more of the native amino acids providing construct-forming activity as described further below.

A "peptidomimetic" is a synthetic chemical compound that has substantially the same structure and/or functional characteristics of a tropoelastin for use in the present invention. A peptidomimetic generally contains at least one residue that is not naturally synthesised. Non-natural components of peptidomimetic compounds may be according to one or more of: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, for example, a beta turn, gamma turn, polyproline turn, beta sheet, alpha helix conformation, and the like.

Peptidomimetics can be synthesized using a variety of procedures and methodologies described in the scientific and patent literatures (for example, Gilman et al., al-Obeidi et al. (1998), Hruby et al. (1997) and Ostergaard & Holm (1997)).

Preferably, the functionally-active fragment is about 100 amino acids in length. Generally, the shortest fragment for use in the present invention will be about 10 amino acids in length. Therefore, the fragment may be between about 10 and about 100 amino acids in length. Shorter fragments are advantageous where, for example, the fragments are sought to be made by synthetic techniques because the preparation of long fragments by, for example, solid-phase synthesis, can be difficult to achieve. Fragments are generally synthesised in vitro where very pure products are desired to be obtained. The advantage of longer fragments is that the hydrophobic/hydrophilic nature of the fragment can be more easily fine-tuned, as can its elastic properties. Preferably, the functionally-active fragment or variant has at least approximately 60% identity to a peptide such as described above, more preferably at least approximately 65%, 66%, 67%, 68%, 69%, 70%, 71%, 72%, 73%, 74%, 75%, 76%, 77%, 78%, 79%, 80%, 81%, 82%, 83%, 84% or 85% identity, even more preferably 90% identity, even more preferably at least approximately 95%, 96%, 97%, 98% 99% or 100% identity. The functionally-active fragment or variant may correspond to, or have identity with, a contiguous sequence of amino acids from the tropoelastin, however it is also contemplated that a functionally-active fragment corresponds to, or has identity with, sequences of amino acids that are clustered spatially in the three-dimensional structure of the tropoelastin.

Such functionally-active fragments and variants include, for example, those having conservative amino acid substitutions. Those skilled in the art can determine appropriate parameters for measuring alignment, including any algorithms (non-limiting examples described below) needed to achieve maximal alignment over the full-length of the sequences being compared. When amino acid sequences are aligned, the percent amino acid sequence identity of a given amino acid sequence A to, with, or against a given amino acid sequence B (which can alternatively be phrased as a given amino acid sequence A that has or includes a certain percent amino acid sequence identity to, with, or against a given amino acid sequence B) can be calculated as: percent amino acid sequence identity=(X/Y)×100, where X is the number of amino acid residues scored as identical matches by the sequence alignment program's or algorithm's alignment of A and B, and Y is the total number of amino acid residues in B. If the length of amino acid sequence A is not equal to the length of amino acid sequence B, the percent amino acid sequence identity of A to B will not equal the percent amino acid sequence identity of B to A.

In calculating percent identity, exact matches are counted. The determination of percent identity between two sequences can be accomplished using a mathematical algorithm. A non-limiting example of a mathematical algorithm utilized for the comparison of two sequences is the algorithm of Karlin and Altschul (1990), modified as in Karlin and Altschul (1993). Such an algorithm is incorporated into the BLASTN and BLASTX programs of Altschul et al. (1990). To obtain gapped alignments for comparison purposes, Gapped BLAST (in BLAST 2.0) can be utilized as described in Altschul et al. (1997). Alternatively, PSI-Blast can be used to perform an iterated search that detects distant relationships between molecules. See Altschul et al. (1997) supra. In one preferred embodiment, utilizing BLAST, Gapped BLAST, and PSI-Blast programs, the default parameters of the respective programs (for example, BLASTX and BLASTN) are used. Alignment may also be performed manually by inspection. Another non-limiting example of a mathematical algorithm utilized for the comparison of sequences is the ClustalW algorithm (Higgins et al. (1994)). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the Vector NTI Program Suite (Invitrogen Corporation, Carlsbad, Calif.). After alignment of amino acid sequences with ClustalW, the percent amino acid identity can be assessed. A non-limiting example of a software program useful for analysis of ClustalW alignments is GENEDOC™ or JalView (http://www-.jalview.org/). GENEDOC™ allows assessment of amino acid (or DNA) similarity and identity between multiple proteins. Another non-limiting example of a mathematical algorithm utilized for the comparison of sequences is the algorithm of Myers and Miller (CAB/OS 1988; 4: 11-17). Such an algorithm is incorporated into the ALIGN program (version 2.0), which is part of the GCG Wisconsin Genetics Software Package, Version 10 (available from Accelrys, Inc., 9685 Scranton Rd., San Diego, Calif., USA). In one preferred embodiment, utilizing the ALIGN program for comparing amino acid sequences, a PAM 120 weight residue table, a gap length penalty of 12, and a gap penalty of 4 is used when assessing percentage identity.

The term "conservative amino acid substitutions" refers to the substitution of an amino acid by another one of the same class, the classes being as follows:

Non-polar: Ala, Val, Leu, Ile, Pro, Met, Phe, Trp
Uncharged polar: Gly, Ser, Thr, Cys, Tyr, Asn, Gln
Acidic: Asp, Glu
Basic: Lys, Arg, His.

Other conservative amino acid substitutions may also be made as follows:

Aromatic: Phe, Tyr, His
Proton Donor: Asn, Gln, Lys, Arg, His, Trp
Proton Acceptor: Glu, Asp, Thr, Ser, Tyr, Asn, Gln.

In one embodiment, the monomers have a sequence that has at least 90% sequence identity with the amino acid sequence of human tropoelastin across at least 50 consecutive amino acids.

In one embodiment, the monomers have a sequence that has at least 80% sequence identity with the sequence of human tropoelastin across a consecutive amino acid sequence consisting of VPGVG.

One type of tropoelastin monomer may be used in the present invention, or combinations of different tropoelastin monomers may be used. For example, the combination of tropoelastin monomers can include 1, 2, 3, 4, 5, 6, 7, 9, 10, or more, different types of tropoelastin monomers. In another embodiment, at least 2, at least 3, at least 4, at least 5, at least 6, at least 7, at least 8, at least 9, at least 10 or more, different tropoelastin monomers can be used. In another embodiment, 1 or more, 2 or more, 3 or more, 4 or more, 5 or more, 6 or more, 7 or more, 8 or more, 9 or more, or 10 or more different types of tropoelastin monomers can be used.

In addition, in other embodiments, the tropoelastin monomers are any number or combination of human and/or non-human (e.g. primate, bovine, equine, sheep, goat, pig, dog, cat, or rodent) tropoelastin monomers.

Further, it will be appreciated that varying the ratio and/or identity of each of the tropoelastin monomers present in a combination can generate tropoelastin-based hydrogels with desired elasticity, tensile strength, and shapeability, and that the strength, elasticity, cross-linking potential and other physical and biochemical behavior of tropoelastin polymers can therefore be varied, and possibly controlled, by incorporating various polymorphic forms of tropoelastin into polymeric scaffolds.

In addition, the ratio and/or identity of each of the tropoelastin monomers present in a combination can be varied so as to match the tropoelastin monomers present in the tissue being repaired, replaced, or regenerated.

In one embodiment, the solution is applied to the surface by spraying the solution onto the surface.

The term "surface", as used herein, refers to any object or device that can be used to make a tropoelastin-based polymer construct of complementary shape. For example, the surface may be a flat surface, such that the aggregate forms as a flat film thereon, or may be a mold. Molds are generally understood to be objects or devices that include a hollowed-out portion. This portion can be filled with the solution of tropoelastin monomers, such that when the concentrate is heated, it hardens or sets inside the mold, adopting its shape. The mold may be of any shape desired by a person skilled in the art. For example, the mold may be shaped such that the construct formed therefrom is in the shape of a particular biological tissue to be repaired and/or replaced (for example, cartilage, vascular tissue or bone) or may include a pattern (of channels, grooves, and the like, as discussed further below) that can be used for assay applications. Accordingly, in one embodiment, the surface is provided in the form of a die, mold or cast enabling the elastic material formed by the process to be shaped into a predefined shape.

In one embodiment, an elastic material may form a "surface" to which the solution of tropoelastin monomers may be applied according to the above described process. For example, a first application may result in the formation of an elastic material on a non-proteinaceous surface. A second application may be made to that elastic material formed on the non-proteinaceous surface, resulting in the formation of an elastic material on the elastic material derived from the first application. The process can be repeated multiple times, enabling building of structures, for example by drop-wise application of solutions of tropoelastin monomers.

The present invention also relates to an elastic material formed by a process including:
  providing a solution of tropoelastin monomers;
  applying the solution to a surface; and
  heating the solution on the surface to a temperature sufficient to enable the tropoelastin monomers in the solution to bind to each other to form an aggregate of tropoelastin monomers.

The present invention also relates to a construct including an elastic material formed by heat-assisted association of tropoelastin monomers.

An elastic material may be a three-dimensional polymeric structure that can be used to repair, augment or replace (at least a portion of) a natural tissue of a subject (for example, for veterinary or medical (human) applications). In addition, the elastic material may be incorporated into, or form a part of, a three-dimensional construct. For example, the aggregate may be incorporated, as a layer, into a construct that is used for cartilage repair, or may be incorporated into a stent.

It will be understood by a person skilled in the art that the degree of contact between the tropoelastin monomers in the solution before the heating step can also affect the material's properties. For example, the more concentrated the solution is (in terms of the quantity of tropoelastin present in the concentrate) prior to heating, the more tropoelastin monomers will interact to form the aggregate, and the less elastic the resulting material will be. Therefore, in certain embodiments, the concentration of tropoelastin monomer in the solution may be directly correlated to the polymerisation degree. Other factors may also contribute to the properties of the material and these include, for example, the type of tropoelastin monomer used, the temperature at which the heating step is carried out, and the time over which the heating is carried out, as discussed above.

As mentioned above, the materials described herein may be porous, i.e., the materials may have porosity i.e. a fractional volume of the material may be composed of open space, for example, pores or other openings. Therefore, porosity measures void spaces in a material and is a fraction of volume of voids over the total volume, as a percentage between 0 and 100% (or between 0 and 1) (see, for example, Coulson et al. (1978)). Determination of matrix porosity is well known to a person skilled in the art, for example, using standardized techniques, such as mercury porosimetry and gas adsorption (such as nitrogen adsorption). Generally, porosity of the material can range from 0.5 to 0.99, from about 0.75 to about 0.99, or from about 0.8 to about 0.95. Preferably, porosity of the material is at least 0.75, more preferably at least 0.8, and most preferably at least 0.9.

The porous materials can have any pore size. As used herein, the term "pore size" refers to a diameter or an effective diameter of the cross-sections of the pores. The term "pore size" can also refer to an average diameter or an average effective diameter of the cross-sections of the pores, based on the measurements of a plurality of pores. The effective diameter of a cross-section that is not circular equals the diameter of a circular cross-section that has the same cross-sectional area as that of the non-circular cross-section. The pores can be filled with a fluid such as water or air. In some embodiments, the pores of the material can have a pore size distribution ranging from about 50 nm to about 1000 µm, from about 250 nm to about 500 µm, from about 500 nm to about 250 µm, from about 1 µm to about 200 µm, from about 10 µm to about 150 µm, from about 15 µm to about 125 µm, from about 20 µm to about 100 µm, or from about 40 µm to about 65 µm. In some embodiments, the material can have a pore size of about 12 µm, about 25 µm, about 45 µm, about 50 µm, or about 65 µm. In some embodiments, the material can have a pore size of 11.7±3.3 µm, 23.4±5.8 µm, or 51±9 µm.

It will be understood by a person skilled in the art that pores can exhibit a distribution of sizes around the indicated "size." Unless otherwise stated, the term "size" as used herein refers to the mode of a size distribution of pores, i.e., the value that occurs most frequently in the size distribution.

The pores can be substantially round cross-section or opening. What is meant by "substantially round" is that the ratio of the lengths of the longest to the shortest perpendicular axes of the pore cross-section is less than or equal to about 1.5. Substantially round does not require a line of symmetry. In some embodiments, the ratio of lengths between the longest and shortest axes of the pore cross-section is less than or equal to about 1.5, less than or equal to about 1.45, less than or equal to about 1.4, less than or equal to about 1.35, less than or equal to about 1.30, less than or equal to about 1.25, less than or equal to about 1.20, less than or equal to about 1.15 less than or equal to about 1.1.

Advantageously, the materials of the present invention are elastic. An "elastic" material is one that returns to a particular shape or conformation after a force (such as compression or extension) that has been applied to it has been withdrawn. It is also referred to as resiliently compressible and extendible, mechanically durable, or pliable material of relatively low hysteresis. This material may be referred to as stretchable, tensile, resilient or capable of recoil. For example, the material can have an extensibility of from about 20 to about 400%.

In some embodiments, the material can have an elastic modulus in the range about 1 kPa to about $10^3$ kPa. As used herein, the term "elastic modulus" refers to an object's or substance's tendency to be deformed elastically (i.e., non-permanently) when a force is applied to it. Generally, the elastic modulus of an object is defined as the slope of its stress-strain curve in the elastic deformation region. Specifying how stress and strain are to be measured, including directions, allows for many types of elastic moduli to be defined. Young's modulus (E) describes tensile elasticity, or the tendency of an object to deform along an axis when opposing forces are applied along that axis; it is defined as the ratio of tensile stress to tensile strain. It is often referred to simply as the elastic modulus. It will also be appreciated that the elastic material formed by the process responds elastically to compression. In some embodiments, the material can have an elastic modulus in the range from about 1 kPa to about 1000 kPa. In some embodiments, the material can have an elastic modulus of about 10 kPa, about 100 kPa, or about 200 kPa.

A higher Young's modulus for a given material according to the invention can be achieved by any one of the following:
  heating for a longer period of time, for example 8 to 16 hours
  addition of silk prior to solubilisation of tropoelastin and heating
  addition of linkers These adjustments result in a material having a Young's Modulus of up to 10 mega pascal.

The material of the present invention may be added to water to form a hydrogel. Accordingly, the present invention relates to a hydrogel including an elastic material, wherein the elastic material is formed by a process including:
  providing a solution of tropoelastin monomers;

applying the solution to a surface; and
heating the solution on the surface to a temperature sufficient to enable the tropoelastin monomers in the concentrate to bind to each other to form an aggregate of tropoelastin monomers,
thereby forming the elastic material.

A hydrogel is generally understood as a network of polymer chains (that are hydrophilic) in which water is the dispersion medium. Hydrogels are highly absorbent—they can contain over 99.9% water—and possess a degree of flexibility very similar to natural tissue, due to their significant water content.

Accordingly, a hydrogel including an elastic material or aggregate of the present invention will typically contain a substantial amount of water. However, the amount of water into which the aggregate is added or immersed to form a hydrogel will depend on factors such as the degree of elasticity desired in the hydrogel. That is, the amount of water added to the aggregate may be an amount that is only just sufficient to impart elasticity. Alternatively, a significant amount of water may be added to make the resultant hydrogel highly elastic. A person skilled in the art will understand that the amount of water used will also depend on the elasticity of the aggregate itself (i.e. if the aggregate is already quite elastic, a smaller amount of water will need to be added than if the aggregate is less elastic).

A person skilled in the art will understand that the discussions herein relating to additional components (e.g. cells, pharmaceutically-active ingredients, and the like) of the materials of the present invention, as well as forms of the materials of the present invention (e.g. as tissue engineering constructs and assays) also apply to the constructs and hydrogels comprising the elastic material of the present invention.

Materials described herein can be used for tissue engineering applications. In some embodiments, tissue engineering aims to replace, repair and/or regenerate tissue and/or organ function or to create artificial tissues and organs for transplantation. In general, scaffolds used in tissue engineering mimic the natural extracellular matrix (ECM) and provide support for cell adhesion, migration, and proliferation. Ideally, they allow for differentiated function, new tissue generation, and its three-dimensional organization. Desired characteristics of scaffolds include physical parameters such as mechanical strength and degradability, while biological properties include biocompatibility and the ability to provide a biologically relevant microenvironment. Biodegradable materials are advantageous in some applications (such as tissue regeneration) because after tissue is grown, the resulting structures are made entirely or almost entirely from biological components.

In some embodiments, the materials described herein can be used for many tissue-engineering applications, including growth and/or replacement of vascular tissues, cardiac tissues, bladder, skin, lung, ligament, tendon, endocrine glands, liver, renal tissue, lymph nodes, pancreas, bone, cartilage, and other tissues. In some embodiments, the materials can be used to deliver signals to cells, act as support structures for cell growth and function, and provide space filling.

Exemplary desired shapes of the elastic material, include, but are not limited to sheets, tubes, and any other three-dimensional shape. Elastic materials formed in the shape of a sheet can be used in the preparation of implants, constructs and grafts to provide reparative, replacement, and/or regenerative therapy for dermal tissues, membranes for tooth root coverage procedures, membranous tissues, and the like. Elastic materials formed in the shape of a tube can be used in the preparation of implants, constructs and grafts to provide reparative, replacement, and/or regenerative therapy for arteries, veins, ureters, urethras, nerves, long bones, and the like. Elastic materials formed in the shape of any other three-dimensional object can be used in the preparation of implants, constructs and grafts to provide reparative, replacement, and/or regenerative therapy for organ transplants, bone remodelling or mending, dental implants, or for muscle, tendon, ligament, and cartilage grafts.

In one embodiment, the elastic material may be formed in a shape enabling its use as a pre-cast patch, which may then be sutured or otherwise adhered onto a surface. Examples include a cardiac patch, a dermal patch, or a patch suitable for the cornea.

A biocompatible elastic material formed, cast or molded in the shape of a sheet can be a flat sheet, or a sheet having curvatures to closely match the contours of the injured, damaged, or diseased tissue or organ being repaired, replaced, or regenerated. The sheets may be of any geometrical shape, including but not limited to squares, rectangles, trapezoids, triangles, circles, ellipses, and the like.

Exemplary areas of the sheets include areas of about 1 $mm^2$ to about 1 $m^2$, about 1 $mm^2$ to about 50 $cm^2$, about 1 $mm^2$ to about 25 $cm^2$, about 1 $mm^2$ to about 10 $cm^2$, about 1 $mm^2$ to about 1 $cm^2$, about 1 $cm^2$ to about 1 $m^2$, about 1 $cm^2$ 1 $cm^2$ to about 500 $cm^2$, 1 $cm^2$ to about 250 $cm^2$, 1 $cm^2$ to about 200 $cm^2$, 1 $cm^2$ to about 150 $cm^2$, to about 100 $cm^2$, about 1 $cm^2$ to about 50 $cm^2$, about 1 $cm^2$ to about 25 $cm^2$, about 1 $cm^2$ to about 10 $cm^2$, about 1 $cm^2$ to about 5 $cm^2$, about 1 $cm^2$ to about 2.5 $cm^2$, about 10 $mm^2$ to about 10 $cm^2$, about 0.1 $cm^2$ to about 10 $cm^2$, about 0.1 $cm.^2$ to about 1 $cm^2$, or any intervening range thereof. For example, the range of areas of 1 $cm^2$ to 100 $cm^2$ of an exemplary sheet includes about areas of about 1 $cm^2$, about 5 $cm^2$, about 10 $cm^2$, about 20 $cm^2$, about 30 $cm^2$, about 40 $cm^2$, about 50 $cm^2$, about 60 $cm^2$, about 70 $cm^2$, about 80 $cm^2$, about 90 $cm^2$, and about 100 $cm^2$.

Exemplary degrees of thickness of an elastic material formed, cast or molded in the shape of a sheet, include a range of about 0.1 mm to about 10 mm, about 0.25 mm to about 7.5 mm, about 0.5 mm to about 5 mm, about 0.75 mm to about 2.5 mm, about 1 mm to about 2 mm or any intervening range thereof.

In another embodiment, the thickness can be about 0.1 mm, about 0.25 mm, about 0.5 mm, about 0.75 mm, about 1 mm, about 2 mm, about 3 mm, about 4 mm, about 5 mm, about 7.5 mm, or about 10 mm or more.

An elastic material formed, cast or molded in the shape of a tube can have any desired length, diameter, and thickness such that the size of the scaffold is suitable to repair, replace, and/or regenerate an injured, damaged, or diseased tissue or organ. Exemplary lengths of the tube include about 0.5 cm, about 1 cm, about 2.5 cm, about 5 cm, about 10 cm, about 25 cm, about 50 cm, about 100 cm, about 150 cm, about 200 cm, about 250 cm, about 300 cm, about 350 cm, about 400 cm, about 450 cm, about 500 cm, or longer. Exemplary diameters of the tube include about 0 mm (e.g., a solid fiber), 0.5 mm, about 1 mm, about 1.5 mm, about 2 mm, about 2.5 mm, about 3 mm, about 3.5 mm, about 4 mm, about 4.5 mm, about 5 mm, about 5.5 mm, about 6 mm, about 6.5 mm, about 7 mm, about 7.5 mm, about 8 mm, about 8.5 mm, about 9 mm, about 9.5 mm, about 10 mm, about 11 mm, about 12 mm or more mm in diameter. In a preferred embodiment, a tube of the invention has about 1 mm to about 10 mm diameter.

An elastic material formed, cast or molded in the shape of other three-dimensional objects can have any desired volume and/shape such that the size of the scaffold is suitable to repair, replace, and/or regenerate an injured, damaged, or diseased tissue or organ.

Exemplary volumes of the three-dimensional shape scaffolds of about 100 mm$^3$ to about 5 m$^3$, about 100 mm$^3$ to about 1000 cm$^3$, about 1 cm$^3$ to about 1000 cm$^3$, about 1 cm$^3$ to about 100 cm$^3$, about 1 cm$^3$ to about 10 cm$^3$, about 10 cm$^3$ to about 1000 m$^3$, about 10 cm$^3$ to about 100 cm$^3$, about 500 cm$^3$ to about 1000 cm$^3$, about 100 mm$^3$ to about 5 cm$^3$, about 100 mm$^3$ to about 2.5 cm$^3$, about 1 cm$^3$ to about 5 cm$^3$, about 1 cm$^3$ to about 2.5 cm$^3$, about 750 cm$^3$ to about 1250 cm$^3$, about 850 cm$^3$ to about 1150 cm$^3$, about 950 cm$^3$ to about 1050 cm$^3$, about 900 cm$^3$ to about 1000 cm$^3$, or any intervening range thereof. For example, the range of volumes of 1 cm$^3$3 to 10 cm$^3$ of an exemplary three-dimensional shape includes about volumes of about 1 cm$^3$, about 2 cm$^3$, about 3 cm$^3$, about 4 cm$^3$, about 5 cm$^3$, about 6 cm$^3$, about 7 cm$^3$, about 8 cm$^3$, about 9 cm$^3$, and about 10 cm$^3$. In one embodiment, the scaffold may have a volume of from about 1 to about 100 microlitres.

In some embodiments, the elastic material is in the form of a film. The thickness of the film can range from nanometers to millimeters. For example, film thickness can range from about 1 nm to about 1000 mm. In some embodiments, the film thickness can be from about 1 nm to 1000 nm, from about 1 μm about 1000 μm, from about 1 mm to about 1000 mm. In some embodiments, the film thickness can be from about 500 nm to about 750 μm, from about 750 nm to about 500 μm, from about 1000 nm to about 250 μm, from about 10 μm to about 100 μm, from about 25 μm to about 75 μm. In some embodiments, film thickness ranges from about 10 nm to about 1 mm. In some embodiments, the film thickness can be about 50 μm.

In some embodiments, the elastic material is a foam. Foams can be made from methods known in the art, including, for example, freeze-drying and gas foaming in which water is the solvent or nitrogen or other gas is the blowing agent, respectively.

In some embodiments, the materials can be used to construct complex delivery devices capable of precisely-defined release profiles. This could be achieved through combining drugs or drug delivery devices (i.e. nanoparticles or microparticles) with the materials described herein and using these to construct more complex drug delivery systems. To give but one example, the materials described herein can additionally include a therapeutic agent to be delivered (for example a small molecule, nucleic acid, protein, lipid and/or carbohydrate drug). Such materials can be useful for delivering a drug to a site that has been targeted for tissue regeneration. For example, a material comprising osteoinductive cells, which is administered to a subject for purposes of regenerating new bone, can additionally include one or more bone morphogenetic proteins (BMPs) which, upon their release, can help further stimulate the growth of new bone.

The elastic material described herein can be combined with another material, for example a biomaterial, to form a composite material. The term "biomaterial" as used herein refers in general to biocompatible naturally occurring materials. Exemplary biomaterials include, but are not limited to, biopolymers, sponges, silk, decellularized tissues, and gelatin. The term "biopolymer" as used herein refers to either a naturally occurring polymer, or a synthetic polymer that is compatible with a biological system or that mimics naturally occurring polymers. Exemplary biopolymers include, but are not limited to, oligosaccharides, polysaccharides such as glycosaminoglycans, peptides, proteins, oligonucleotides, nucleic acids, polyketides, peptoids, hydrogels, poly(glycols) such as polyethylene glycol), collagen, silk, and polylactates.

In one embodiment the elastic material may be combined with a salt, or with polyvinyl pyrolidone.

The elastic material of the present invention may also include other components such as pharmaceutically-acceptable excipients and biologically active agents (for example drugs, vitamins and minerals), to assist in repair and/or re-generation of the target tissue, and/or to provide a method of achieving targeted delivery of biologically active compounds. Such components may be added to the tropoelastin solution prior to heating (so that they are incorporated into the elastic material as it forms) or they may be placed into the elastic material after it has formed. In addition, the components may be present in the aqueous solution used to form a hydrogel from the elastic material. A person skilled in the art will understand that where the components to be added are not stable under the conditions required to form the elastic material, the components should be added after the elastic material has already been formed.

Any biologically active agent known to a person skilled in the art to be of benefit in the diagnosis, treatment or prevention of a disease is contemplated as a therapeutic agent in the context of the present invention. Therapeutic agents include hormones, growth factors, enzymes, DNA, plasmid DNA, RNA, siRNA, viruses, proteins, lipids, pro-inflammatory molecules, antibodies, antibiotics, anti-inflammatory agents, anti-sense nucleotides and transforming nucleic acids or combinations thereof. Any of the therapeutic agents can be combined to the extent such combination is biologically compatible.

Suitable growth factors and cytokines include, but are not limited, to stem cell factor (SCF), granulocyte-colony stimulating factor (G-CSF), granulocyte-macrophage stimulating factor (GM-CSF), stromal cell-derived factor-1, steel factor, VEGF, TGFβ, platelet derived growth factor (PDGF), angiopoeltins (Ang), epidermal growth factor (EGF), bFGF, HNF, NGF, bone morphogenic protein (BMP), fibroblast growth factor (FGF), hepatocye growth factor, insulin-like growth factor (IGF-1), interleukin (IL)-3, IL-1α, IL-1β, IL-6, IL-7, IL-8, IL-11, and IL-13, colony-stimulating factors, thrombopoietin, erythropoietin, fit3-ligand, and tumor necrosis factor α (TNFα). Other examples are described in Dijke et al. (1989); Mulder et al. (1998); Ziegler et al. (1997). Suitable hormones include, but are not limited to, antimullerian hormone (or mullerian inhibiting factor or hormone), adiponectin, adrenocorticotropic hormone (or corticotropin), angiotensinogen and angiotensin, antidiuretic hormone (or vasopressin, arginine vasopressin), atrial-natriuretic peptide (or atriopeptin), calcitonin, cholecystokinin, corticotropin-releasing hormone, erythropoietin, follicle-stimulating hormone, gastrin, ghrelin, glucagon, gonadotropin-releasing hormone, growth hormone-releasing hormone, human chorionic gonadotropin, human placental lactogen, growth hormone, insulin-like growth factor 1, insulin-like growth factor (or somatomedin), leptin, luteinizing hormone, melanocyte stimulating hormone MSH, orexin, oxytocin, parathyroid hormone, prolactin, relaxin, secretin, somatostatin, thrombopoletin, thyroid-stimulating hormone (or thyrotropin), and thyrotropin-releasing hormone.

Exemplary pharmaceutically active compounds (for example, therapeutic agents) include, but are not limited to, those found in Harrison et al., Physicians Desk Reference, Pharmacological Basis of Therapeutics (1990), United States Pharmacopeia, current edition of Goodman and Oilman's *The Pharmacological Basis of Therapeutics*; and current edition of *The Merck Index*.

In another embodiment, the elastic material (or hydrogel formed therefrom) includes a population of multipotent or pluripotent stem cells (discussed further below), and hormones, growth factors, cytokines, morphogens (e.g., retinoic acid etc), extracellular matrix materials (e.g., fibronectin, laminin, collagen, etc.) or other materials (e.g., DNA, viruses, other cell types, etc.) that facilitate the differentiation of the cell population along a particular developmental pathway once the elastic material or hydrogel has been implanted in the patient. Alternatively, or in addition, the cells may be differentiated in vitro during cell culturing with the elastic material or hydrogel.

The bioactive agent can be covalently linked to the elastic material through a linker. The linker can be a cleavable linker or non-cleavable linker, depending on the application. As used herein, a "cleavable linker" refers to linkers that are capable of cleavage under various conditions. Conditions suitable for cleavage can include, but are not limited to, pH, UV irradiation, enzymatic activity, temperature, hydrolysis, elimination and substitution reactions, redox reactions, and thermodynamic properties of the linkage. In many cases, the intended nature of the conjugation or coupling interaction, or the desired biological effect, will determine the choice of linker group.

Pharmaceutically-acceptable excipients include any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Gennaro (2006) discloses various excipients used in formulating pharmaceutical compositions and known techniques for the preparation thereof. Except insofar as any conventional excipient is incompatible with a substance or its derivatives, such as by producing any undesirable biological effect or otherwise interacting in a deleterious manner with any other component(s) of the hydrogel, its use is contemplated to be within the scope of this invention.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in the tropoelastin-containing solutions. Excipients such as colouring agents, coating agents, sweetening, flavouring, and perfuming agents can be present in the solution, according to the judgment of the formulator. General considerations in the formulation and/or manufacture of pharmaceutical agents may be found, for example, in Gennaro (2006).

The amount of tropoelastin and biologically active agent present in the material will necessarily depend upon the particular drug and the condition to be treated. A person skilled in the art will be aware of appropriate agents and amounts to use to treat the condition.

A therapeutically effective amount of a material of the present invention may be delivered to a patient and/or organism prior to, simultaneously with, and/or after diagnosis with a disease, disorder, and/or condition. In some embodiments, a therapeutically-effective amount of a material of the present invention is delivered to a patient and/or organism prior to, simultaneously with, and/or after onset of symptoms of a disease, disorder, and/or condition.

The term "therapeutically-effective amount", as used herein, refers to an amount of the material of the present invention that is sufficient to treat, alleviate, ameliorate, relieve, delay onset of, inhibit progression of, reduce severity of, and/or reduce incidence of one or more symptoms or features of the disease, disorder, and/or condition.

As mentioned above, materials of the present invention can be used for tissue engineering applications. In some embodiments, tissue engineering aims to replace, repair and/or regenerate tissue and/or organ function or to create artificial tissues and organs for transplantation. In general, scaffolds used in tissue engineering (for example hydrogel scaffolds) mimic the natural ECM and provide support for cell adhesion, migration, and proliferation. Ideally, they allow for differentiated function, new tissue generation, and its three-dimensional organization. Desired characteristics of elastic scaffolds include physical parameters such as mechanical strength and degradability, while biological properties include biocompatibility and the ability to provide a biologically relevant microenvironment. Biodegradable materials are advantageous because after tissue is grown, the resulting structures are made entirely or almost entirely from biological components.

In some embodiments, materials to be utilized for drug delivery can be altered in ways that result in enhanced residence times, sustained drug delivery and/or targeted drug delivery. The material properties, such as permeability (for example, sustained-release applications), enviro-responsive nature (for example, pulsatile-release applications), surface functionality (for example, PEG coatings for stealth release), biodegradability (for example, bioresorbable applications), and surface biorecognition sites (for example, targeted release and bioadhesion applications), can be altered and/or optimized for controlled drug-delivery applications. For example, by controlling tropoelastin chain length, tropoelastin composition and/or tropoelastin concentration, it is possible to control the density of the material. Control over the density provides, among other things, control over sustained-release properties of the resulting material.

In some embodiments, enzymes can be encapsulated within the materials to create drug delivery systems that are responsive to biological analytes.

The elastic materials described herein can additionally include one or more additives. Additives can be resolving (biodegradable) polymers, mannitol, starch sugar, inosite, sorbitol, glucose, lactose, saccharose, sodium chloride, calcium chloride, amino acids, magnesium chloride, citric acid, acetic acid, hydroxyl-butanedioic acid, phosphoric acid, glucuronic acid, gluconic acid, poly-sorbitol, sodium acetate, sodium citrate, sodium phosphate, zinc stearate, aluminium stearate, magnesium stearate, sodium carbonate, sodium bicarbonate, sodium hydroxide, polyvinylpyrolidone, polyethylene glycols, carboxymethyl celluloses, methyl celluloses, starch, micro-particles, nano-particles, aprotinin, Factor XIII, or their mixtures. Without wishing to be bound by a theory, one or more additives in the material can alter (for example reduce or increase) the rate of degradation of the material.

In some embodiments, the materials described herein can be utilized for in vitro tissue culture applications. In certain embodiments, the materials described can be utilized to develop assays that are useful for drug discovery and biological studies (for example, assemble arrays of well-defined materials for high-throughput drug screening). For example, the presence of feeder cells (for example, endothelial cells or fibroblasts) in the presence of functional cells (for example, hepatocytes) can be used to increase the maintenance of the functional cell type. Thus, it is possible to generate three-dimensional structures that mimic the native structure of functional organs that can be subsequently used for drug discovery and/or diagnostics assays.

A person skilled in the art will understand that where the cells to be incorporated into the elastic material are not stable under the conditions required to form the elastic material, the cells should be added after the elastic material has already been formed. For example, the cells may be present in the aqueous solution used to form a hydrogel from the elastic material.

In some embodiments, the materials described herein can be utilized for toxicity assays that can test the toxicity of a test substance (for example, utilizing materials in which liver cells have been encapsulated).

In some embodiments, the materials described herein can be used to make and coat various structures, such as microfluidic channels. In this approach, the walls of the microchannels can be made from construct assemblies instead of from more commonly-used materials such as polystyrene, glass and PDMS. Microfluidic channels made from construct assemblies could be useful for many purposes, for example, in applications where it is desirable for the walls of the microfluidic channel to attract and bind cells.

In some embodiments, the materials described herein can be used for diagnostic applications. To give but one example, cell-laden materials can be used for generating tissue-like materials and/or material assemblies that can be used in assays which test for the presence of one or more particular microbes. For example, if a microbe (for example, bacteria, viruses, fungi, etc.) were known to specifically bind to a particular tissue, then tissue-like materials could be fabricated that would test for the presence of the microbe in the sample.

The materials described herein may be patterned (e.g. a micropatterned elastic material). Micropatterned materials can be prepared using, for example, a method including contacting a tropoelastin solution with a surface of a mold, the mold including, on at least one surface thereof, a three-dimensional negative configuration of a predetermined micropattern to be disposed on and integral with at least one surface of the elastic material, and heating the solution while in contact with the micropatterned surface of the mold, thereby providing a micropatterned elastic material. Elastic materials prepared this way include a predetermined and designed micropattern on at least one surface of the material, which pattern is effective to facilitate cell alignment, tissue repair, growth or regeneration, or is effective to provide delivery of a protein or a therapeutic agent. The micropattern geometry can be controlled using the molds of the appropriate pattern or size. Further, the micropattern can be characterized for surface morphology by known techniques, such as field emission scanning electron and atomic force microscopy.

In some embodiments, the micropattern is in the forms of grooves or channels. The groove size (width) can range from about 500 nm to about 500 µm. In some embodiments, the groove size can range from about 1 µm to about 250 µm, from about 10 µm to about 100 µm, or from about 20 µm to about 75 µm. In some embodiments, the groove size is about 50 µm or about 20 µm.

The spacing between the grooves can also be optimized for desired use. For example, spacing between the grooves can range from about 500 nm to about 500 µm. In some embodiments, the distance between the grooves can range from about 1 µm to about 250 µm, from about 10 µm to about 100 µm, or from about 20 µm to about 75 µm. In some embodiments, the distance between the grooves is about 50 µm or about 20 µm.

The groove-thickness depth can range from about 250 nm to about 500 µm. In some embodiments, groove thickness can range from about 500 nm to about 250 µm, or from about 750 nm to about 1000 nm.

As mentioned above, the elastic materials described herein can be used in tissue engineering and repair. As used herein, the term "repair" refers to any correction, reinforcement, reconditioning, remedy, making up for, making sound, renewal, mending, patching, or the like that restores function. Accordingly, the term "repair" can also mean to correct, to reinforce, to recondition, to remedy, to make up for, to make sound, to renew, to mend, to patch or to otherwise restore function.

It will be understood by a person skilled in the art that hydrogels formed from the elastic materials of the present invention can be used in tissue engineering and repair as well. Therefore, where the elastic material of the present invention is mentioned in these contexts, it will be understood that, where appropriate, hydrogels formed from the materials can be utilised in addition to, or as an alternative to, the elastic materials themselves. It will also be understood by a person skilled in the art that hydrogels can form from the elastic materials simply by contact of the elastic materials with physiological conditions by virtue of the elastic material absorbing water from the surrounding environment.

By "treatment", "prevention," or "amelioration" is meant delaying or preventing the onset, reversing, alleviating, ameliorating, inhibiting, slowing down or stopping the progression, aggravation, deterioration, or the progression of severity of a condition associated with a disease or disorder.

The elastic materials of the present invention may be administered using any amount and any route of administration effective for treatment. The exact amount required will vary from subject to subject, depending on the species, age, and general condition of the subject, the severity of the infection, the particular hydrogel, its mode of administration, its mode of activity, and the like.

In another embodiment, the elastic materials described herein are used in regenerative medicine for osteopathic applications, including, but not limited to craniofacial, odontic, and periodontic applications. In one embodiment, a construct or device including an elastic material (or hydrogel formed from an elastic material), is provided for use in reconstruction and regeneration of oral and craniofacial tissues.

In particular embodiments, the elastic material (or hydrogel formed from the elastic material) includes one or more tropoelastin monomers, and human collagen. The resulting materials and hydrogels are engineered for the desired surface topography, porosity, strength and elasticity. In some embodiments, the elastic material or hydrogel does not contain proteins or polypeptides other than tropoelastin.

In one embodiment, the elastic material is cast in the form of a sheet and can be used as a regenerative membrane in various clinical applications, e.g., guided tissue regeneration (GTR) or root coverage procedures. In one embodiment, the elastic material is cast as a sheet and seeded with periodontal ligament cells (PDL) forming an implant or graft that is suitable for use in a root coverage procedure. Once the implant has formed, a surgeon engrafts the implant in a root coverage procedure using methods known to a person skilled in the art.

In another embodiment, the elastic material is cast in a three-dimensional shape for use as a bone filling material. Virtually any shape can be achieved because the pre-heated solution is in a shapeable form. Once placed into a mold or into the desired area, the solution can be "hardened" by heating. In addition, the material can support unique clinical applications in periodontal medicine for guided bone regeneration (GBR) procedures and eliminate the need for a bone filler and a membrane to contain the bone graft.

In a particular embodiment, the elastic material (or hydrogel formed from the material), or an implant comprising the elastic material or hydrogel formed from the material, is molded into a desired shape, and includes one or more populations of cells.

In general, cells to be used in accordance with the present invention are any types of cells. The cells should be viable when incorporated in the elastic materials of the present invention (or hydrogels formed from the elastic materials). In some embodiments, suitable cells include, but are not limited to, mammalian cells (for example human cells, primate cells, mammalian cells, rodent cells, etc), avian cells, fish cells, insect cells, plant cells, fungal cells, bacterial cells, and hybrid cells. In some embodiments, exemplary cells include stem cells, totipotent cells, pluripotent cells, and/or embryonic stem cells. In some embodiments, exemplary cells include, but are not limited to, primary cells and/or cell lines from any tissue. For example, cardiomyocytes, myocytes, hepatocytes, keratinocytes, melanocytes, neurons, astrocytes, embryonic stem cells, adult stem cells, hematopoietic stem cells, hematopoietic cells (for example monocytes, neutrophils, macrophages, etc), ameloblasts, fibroblasts, chondrocytes, osteoblasts, osteoclasts, neurons, sperm cells, egg cells, liver cells, epithelial cells from lung, epithelial cells from gut, epithelial cells from intestine, liver, epithelial cells from skin, etc, and/or hybrids thereof, may be used in accordance with the present invention.

Exemplary mammalian cells include, but are not limited to, human umbilical vein endothelial cells (HUVEC), Chinese hamster ovary (CHO) cells, HeLa cells, Madin-Darby canine kidney (MDCK) cells, baby hamster kidney (BHK cells), NS0 cells, MCF-7 cells, MDA-MB-438 cells, U87 cells, A172 cells, HL60 cells, A549 cells, SP10 cells, DOX cells, DG44 cells, HEK 293 cells, SHSY5Y, Jurkat cells, BCP-1 cells, COS cells, Vero cells, GH3 cells, 9L cells, 3T3 cells, MC3T3 cells, C3H-10T1/2 cells, NIH-3T3 cells, and C6/36 cells.

In a certain embodiment, the one or more cell populations include bone marrow stem cells, mesenchymal stem cells, or pre-osteoblast cells to facilitate tissue or bone regeneration. Additionally, the osteogenic potential of the material/hydrogel/implant can be used as a sole therapy or in combination with currently available commercial bone filler products or primary autologous bone harvests. A person skilled in the art will recognize that any type of bones can be repaired, replace, or regenerated using the foregoing techniques.

In some embodiments, the conditions under which cells are included in the elastic materials (or hydrogels formed therefrom) are altered in order to maximize cell viability. In some embodiments, conditions (for example pH, ionic strength, nutrient availability, temperature, oxygen availability, osmolarity, etc) of the surrounding environment may need to be regulated and/or altered to maximize cell viability.

Cell viability can be measured by monitoring one of many indicators of cell viability. In some embodiments, indicators of cell viability include, but are not limited to, intracellular esterase activity, plasma membrane integrity, metabolic activity, gene expression, and protein expression. To give but one example, when cells are exposed to a fluorogenic esterase substrate (for example calcein AM), live cells fluoresce green as a result of intracellular esterase activity that hydrolyzes the esterase substrate to a green fluorescent product. To give another example, when cells are exposed to a fluorescent nucleic acid stain (for example ethidium homodimer-1), dead cells fluoresce red because their plasma membranes are compromised and, therefore, permeable to the high-affinity nucleic acid stain.

In general, the percent of cells in the material (or the hydrogel formed therefrom) is a percent that allows for the formation of elastic materials and/or hydrogels in accordance with the present invention. In some embodiments, the percent of cells that is suitable ranges between about 0.1% w/w and about 80% w/w, between about 1.0% w/w and about 50% w/w, between about 1.0% w/w and about 40% w/w, between about 1.0% w/w and about 30% w/w, between about 1.0% w/w and about 20% w/w, between about 1.0% w/w and about 10% w/w, between about 5.0% w/w and about 20% w/w, or between about 5.0% w/w and about 10% w/w. In some embodiments, the percent of cells in a solution that is suitable for forming elastic materials in accordance with the present invention is approximately 5% w/w. In some embodiments, the concentration of cells in an aqueous solution that is suitable for forming hydrogels in accordance with the invention ranges between about $1 \times 10^5$ cells/mL and $1 \times 10^8$ cells/mL or between about $1 \times 10^6$ cells/mL and $1 \times 10^7$ cells/mL. In some embodiments, a single elastic material r hydrogel formed therefrom includes a population of identical cells and/or cell types. In some embodiments, a single elastic material or hydrogel formed therefrom includes a population of cells and/or cell types that are not identical. In some embodiments, a single elastic material or hydrogel formed therefrom may include at least two different types of cells. In some embodiments, a single elastic material or hydrogel formed therefrom may include 3, 4, 5, 10, or more types of cells.

Any of a variety of cell culture media, including complex media and/or serum-free culture media, that are capable of supporting growth of the one or more cell types or cell lines may be used to grow and/or maintain cells. Typically, a cell culture medium contains a buffer, salts, energy source, amino acids (for example, natural amino acids, non-natural amino acids, etc), vitamins, and/or trace elements. Cell culture media may optionally contain a variety of other ingredients, including but not limited to, carbon sources (for example, natural sugars, non-natural sugars, etc), cofactors, lipids, sugars, nucleosides, animal-derived components, hydrolysates, hormones, growth factors, surfactants, indicators, minerals, activators of specific enzymes, activators inhibitors of specific enzymes, enzymes, organics, and/or small molecule metabolites. Cell culture media suitable for use in accordance with the present invention are commercially available from a variety of sources, for example, ATCC (Manassas, Va.). In certain embodiments, one or more of the following media are used to grow cells: RPMI-1640 Medium, Dulbecco's Modified Eagle's Medium, Minimum Essential Medium Eagle, F-12K Medium, Iscove's Modified Dulbecco's Medium.

As discussed above, one significant advantage of the invention is the development of materials (and corresponding hydrogels) with unique properties, e.g., tensile strength, elasticity, and flexibility/stiffness, generated by combining 2, 3, 4, 5, 6, 7, 8, 9, 10 or more individual tropoelastin isoforms, themselves having unique properties. Such unique materials (and the corresponding hydrogels) can be tailored for use at locations in the body where their unique properties are the most advantageous. For example, the strongest fibers can be used to repair muscles, the most elastic fibers can be used to construct bladders and other flexible organs (e.g. blood vessels and cardiac tissues), and the stiffest fibers can be used in cartilage repair.

The present invention also relates to a method of repairing and/or restoring biological tissue, the method comprising administration of a therapeutically effective amount of an elastic material of the present invention to a subject in need thereof.

The present invention also relates to the use of a therapeutically effective amount of an elastic material of the present invention, for repairing and/or restoring biological tissue.

In one embodiment, the invention provides an elastic material of the present invention, when used in a method of repairing and/or restoring biological tissue.

The present invention also relates to the use of a therapeutically effective amount of an elastic material of the present invention, for the repair and/or restoration of biological tissue. The invention also includes use of this material for the manufacture of a medicament for the repair and/or restoration of biological tissue.

As mentioned above, it will be appreciated that, in these embodiments, a hydrogel formed from the elastic material of the present invention can be used as an alternative to the elastic material, provided that it is then treated appropriately (by, for example, exposure to water) to form a hydrogel.

The present invention also relates to a method of repairing and/or restoring biological tissue comprising the steps of:
- identifying a subject having tissue injury; and
- administering to the subject a therapeutically effective amount of the elastic material of the present invention,
- administering to the subject a therapeutically effective amount of a hydrogel formed from the elastic material of the present invention, or
- administering to the subject an amount of the elastic material of the present invention to form a therapeutically effective amount of the hydrogel, followed by treating the elastic material of the present invention to form the hydrogel.

The present invention also relates to a method of accelerating repair and/or restoration of biological tissue comprising administering to a subject in need thereof:
- a therapeutically effective amount of the elastic material of the present invention,
- a therapeutically effective amount of a hydrogel formed from the elastic material of the present invention, or
- an amount of the elastic material of the present invention to form a therapeutically effective amount of the hydrogel, followed by treating the elastic material to form the hydrogel.

Elastic materials of the present invention, and hydrogels formed therefrom, are typically formulated in dosage unit form for ease of administration and uniformity of dosage. It will be understood, however, that the total daily usage of the materials and/or hydrogels of the present invention will be decided by the attending physician within the scope of sound medical judgment.

The specific therapeutically effective dose level for any particular subject or organism will depend upon a variety of factors including the disorder being treated and the severity of the disorder; the activity of the specific active ingredient employed; the specific polymer and/or cells employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The materials of the present invention (and hydrogels formed therefrom) may be administered by any route. In some embodiments, the materials of the present invention are administered by a variety of routes, including direct administration to an affected site. For example, materials (and/or hydrogels formed therefrom) may be administered locally near a site which is in need of tissue regeneration.

In certain embodiments, the elastic materials of the present invention (and/or hydrogels formed therefrom) may be administered such that included cells and/or therapeutic agents to be delivered are released at concentrations ranging from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic effect. The desired dosage may be delivered, for example, three times a day, two times a day, once a day, every other day, every third day, every week, every two weeks, every three weeks, or every four weeks. In certain embodiments, the desired dosage may be delivered using multiple administrations (for example, two, three, four, five, six, seven, eight, nine, ten, eleven, twelve, thirteen, fourteen, or more administrations).

In some embodiments, the present invention encompasses "therapeutic cocktails" comprising the elastic materials of the present invention (and/or hydrogels formed therefrom). In some embodiments, the materials include a single cell type and, optionally, a therapeutic agent. In some embodiments, materials include multiple different cell types and, optionally, a therapeutic agent.

It will be appreciated that cell-laden elastic materials in accordance with the present invention (and hydrogels formed therefrom) can be employed in combination therapies. The particular combination of therapies (therapeutics or procedures) to employ in a combination regimen will take into account compatibility of the desired therapeutics and/or procedures and the desired therapeutic effect to be achieved. It will be appreciated that the therapies employed may achieve a desired effect for the same purpose (for example, a hydrogel comprising a certain cell type to be used to promote tissue growth may be administered concurrently with another therapeutic agent used to stimulate growth of the same tissue), or they may achieve different effects (for example, control of any adverse effects, such as inflammation, infection, etc).

The invention provides a variety of kits comprising one or more of the materials of the present invention. For example, the invention provides a kit comprising an elastic material and instructions for use. A kit may include multiple different elastic materials. A kit may optionally include tropoelastin monomers, a concentrated solution of tropoelastin monomers, associated tropoelastin monomers, biologically-active compounds, and the like. A kit may include any of a number of additional components or reagents in any combination. All of the various combinations are not set forth explicitly but each combination is included in the scope of the invention. A few exemplary kits that are provided in accordance with the present invention are described in the following paragraphs.

According to certain embodiments of the invention, a kit may include, for example, (i) a solution of tropoelastin monomers; (ii) a mold; and (iii) instructions for heating and forming an elastic material from the solution.

A kit may also include, for example, (i) concentrate of tropoelastin monomers; (ii) a mold; and (iii) instructions for forming an elastic material from the concentrate.

Kits may further include other materials desirable from a commercial and user standpoint, including other buffers, diluents, filters, needles, and syringes.

Kits typically include instructions for use of the materials of the present invention. Instructions may, for example, include protocols and/or describe conditions for production of elastic materials, administration of the materials to a subject in need thereof, production of material assemblies, etc. Kits will generally include one or more vessels or containers so that some or all of the individual components and reagents may be separately housed. Kits may also include a means for enclosing individual containers in relatively close confinement for commercial sale, for example, a plastic box, in which instructions, packaging materials such as styrofoam, etc, may be enclosed.

The kit or "article of manufacture" may include a container and a label or package insert on or associated with the container. Suitable containers include, for example, bottles, vials, blister packs, etc. The containers may be formed from a variety of materials such as glass or plastic. The label or package insert indicates that the construct or composition is used for treating the condition of choice. In one embodiment, the label or package insert includes instructions for use and indicates that the therapeutic composition can be used to repair or regenerate tissue.

EXAMPLES

Example 1—Use of Water as Solvent for Tropoelastin 100 mg tropoelastin dissolved in 333 µl water at 4° C. Used a 1 ml 31 gauge syringe to place a drop of tropoelastin solution onto a glass slide. Placed at 160° C. for 1 minute. Added a further drop of tropoelastin; left for 1 min before adding a further drop. Repeated approximately 10 times. Left at 160° C. for 4 h. Material turned glassy and darkish brown (A). Placed in PBS—slowly wetted, did not dissolve and became quite elastic (B).

Example 2—Use of HFP as Solvent for Tropoelastin 100 mg tropoelastin dissolved in 500 µL 1,1,1,3,3,3-hexafluoro-2-propanol (HFP) overnight at room temp. Used a 1 mL 31 gauge syringe to place drops of tropoelastin solution onto a glass slide sitting on top of a heating block set at 70° C. Placed at 160° C. for 4 h. Material appeared to bubble in oven and turned glassy and brown (A). Placed in PBS—slowly wetted, became soft and elastic, appeared to have gas bubbles caught within the material (B).

Example 3—Use of 70% EtOH as Solvent for Tropoelastin

Dissolved 100 mg tropoelastin in 650 µl 70% EtOH (154 mg/mL). Used a 1 ml 31 gauge syringe to place drops of tropoelastin solution onto a glass slide sitting on top of a heating block set at 85° C. Could build up 3D structure of drop upon drop by waiting ~1 min between each drop. Placed at 160° C. oven for 4 h. Material appeared to bubble in oven and turned glassy and darkish brown.

Example 4—Coating an Inanimate Object

20% w/v tropoelastin in HFP used to coat piece of Tygon tubing by repeated dipping into the solution. Coated tube placed at 160° C. for 4 h. Tropoelastin solution became hard and glass like and could not be removed from tubing. Wet with PBS. Material became soft and elastic, it could be peeled off the tubing and did not dissolve.

Example 5—Electrospinning

Electrospun 20% (w/v) tropoelastin in HFP, 1 mL/h, ~17 cm from syringe tip to collector, 20 kV(+)/grounded, 0.1 ml solution, collector-aligned wires 2 cm apart 4 cm long. Placed at 160° C. for 24 h. Wet with PBS did not dissolve; went gel-like, maintained shape. Checked by SEM.

Example 6—Dermal Human Fibroblast Growth In Vitro on Heat-Treated Electrospun Tropoelastin 20% (w/v) tropoelastin in HFP was electrospun as described above. Human neonatal dermal fibroblasts (NHF8909; $5 \times 10^5$ cells/well) were seeded onto heat-treated electrospun aligned fibers that were anchored to plastic coverslips within 6 well plates. Following 48 h culture in DMEM+10% FBS+Pen/Strep at 37° C. in 5% $CO_2$ the samples were prepared for SEM analysis. Samples were fixed with 2% glutaraldehyde in 0.1 M sodium cacodylate/0.1 M sucrose, post-fixed with 1% osmium, dehydrated in increasing concentrations of ethanol mounted and gold coated. Heat-treated electrospun tropoelastin supported cell attachment, spreading and proliferation.

Example 7—Subcutaneous Implantation of Heat-Treated Electrospun Tropoelastin in Mice Non-aligned electrospun tropoelastin constructs were prepared using 20% tropoelastin in HFP. Samples were spun at 20 kV onto a round collector (non-aligned) at a distance of 17 cm, 1 mL/hr rate. 0.2 ml solution was used per construct. Placed at 160° C. for 22 h.

Each mouse was implanted with one heat-treated non-aligned electrospun tropoelastin construct and one Integra control. Two mice for each time point at 1 week, 3 weeks and 6 weeks. Subcutaneous implantation was performed with two 10 mm incisions which were made on the back of each mouse and dissected to create subcutaneous pouches. Electrospun scaffolds or Integra scaffold (Integra Life-Sciences Corporation) without an outer silicone layer were inserted into each pouch. The wounds were then closed with 6-0 silk sutures and covered using IV3000 wound dressings (Smith & Nephew) for 5 days. Carprofen (5 mg/kg) was given at the time of anesthesia and then on the following day post surgery for analgesia. After surgery, each mouse was caged individually for the first two days and then two mice per cage thereafter with free access to water and food. Skin biopsies were collected for histological analysis at 1, 3 and 6 weeks post-implantation. Explanted scaffolds and surrounding skin were stained with Verhoeff-Van Gieson (VVG), demonstrating the elastic nature of the implant.

Heat-treated electrospun tropoelastin persisted in mice for a minimum of 6 weeks post implantation.

Example 8—Heat-Treated Water-Based Tropoelastin Films 100 mg tropoelastin dissolved in 1 ml water at 4° C. Solution pipetted into wells of an 8-well glass chamber slide. Solution was concentrated and dried by placing at 37° C. for 16 h. Samples were further heated to 160° C. for 4 h. After heating at 37° C. the scaffolds are translucent and light brown. Following 160° C. heating the samples are still translucent but darker in colour.

Example 9—Micropatterned Heat-Treated Water-Based Tropoelastin Films 70 mg tropoelastin dissolved in 1 ml water at 4° C. Solution pipetted onto a PEWS (polydimethylsiloxane) mould containing 3.5 µm wide, and 500 nm, deep ridges. Solution was concentrated and dried by placing at 37° C. for 16 h. Samples were further heated to 160° C. for 4 h. Images were obtained using a light microscope with 20× and 40× objectives.

REFERENCES al-Obeidi, F. et al. Peptide and peptidomimetic libraries: molecular diversity and drug design. *Mol Biotechnol* 9(3), 205-223 (1998).
Altschul, S. F. et al. Basic local alignment search tool. *J Mol Biol* 215(3), 403-410 (1990).
Altschul, S. F. et al. Gapped BLAST and PSI-BLAST: a new generation of protein database search programs. *Nucleic Acids Res* 25(17), 3389-3402 (1997).
Anderson, et al. Nanoliter-scale synthesis of arrayed biomaterials and application to human embryonic stem cells. *Nature Biotechnology* 22, 863-866 (2004).
Anderson, et al. Biomaterial microarrays: rapid, microscale screening of polymer-cell interaction. *Biomaterials* 26. 4892-4897 (2005).
Coulson J. M. et. al., *Chemical Engineering*, 1978, volume 2, 3rd Edition, Pergamon Press, 126.
Dijke et al. Growth factors for wound healing. Bio/Technology 7, 793-798 (1989).
Falsey, et al. Peptide and small molecule microarray for high throughput cell adhesion and functional assays. *Bioconjugate Chemistry* 12, 346-353 (2001).
Gennaro, A. R., *Remington: The Science and Practice of Pharmacy*, 21st ed. (2006), Lippincott Williams & Wilkins.
Gilman et al. (eds) Organic Syntheses Collective Volumes, John Wiley & Sons, Inc., NY.
Harrison, T. R. et al. (eds) *Harrison's Principles of Internal Medicine*, 13th Edition, McGraw-Hill N.Y., NY.
Higgins, D. G. et al. CLUSTAL W: improving the sensitivity of progressive multiple sequence alignment through sequence weighting, position-specific gap penalties and weight matrix choice. *Nucleic Acids Res* 22(22), 4673-4680 (1994).
Hruby, V. J. et al. Synthesis of oligopeptide and peptidomimetic libraries. *Curr Opin Chem Biol* 1 (1), 114-119 (1997).
Karlin, S. & Altschul, S. F. Methods for assessing the statistical significance of molecular sequence features by using general scoring schemes. *Proc Natl Acad Sci USA* 87(6), 2264-2268 (1990).
Karlin, S. & Altschul, S. F. Applications and statistics for multiple high-scoring segments in molecular sequences. *Proc Natl Acad Sci USA* 90(12), 5873-5877 (1993).
Miyamoto, K. et al. Creation of cross-linked electrospun isotypic-elastin fibers controlled cell-differentiation with new cross-linker. *Int J Biol Macromolecules* 45, 33-41 (2009).
Li, M. et al. Electrospun protein fibers as matrices for tissue engineering. *Biomaterials* 26(30), 5999-6008 (2005).
Li, M. et al. Electrospinning polyaniline-contained gelatin nanofibers for tissue engineering applications. *Biomaterials* 27(13), 2705-2715 (2006).
Liu, et al. Nanostructured materials designed for cell binding and transduction. *Biomacromolecules* 2(2), 362-368 (2001).
Mulder G D, Haberer P A, Jeter K F (eds). Clinicians' Pocket Guide to Chronic Wound Repair. 4th ed. Springhouse, Pa.: Springhouse Corporation; 1998:85.
Orner, et al. Arrays for the combinatorial exploration of cell adhesion. *Journal of the American Chemical Society* 126, 10808-10809 (2004).
Ostergaard, S. & Holm, A. Peptomers: a versatile approach for the preparation of diverse combinatorial peptidomimetic bead libraries. *Mol Divers* 3(1), 17-27 (1997).
Pharmacological Basis of Therapeutics, 8th Edition, Goodman and Gilman, 1990.
Physicians Desk Reference, 50th Edition, 1997, Oradell N.J., Medical Economics Co.
Taurniare, G. et al. Polymer microarrays for cellular adhesion. *Chem Comm* 2118-2120 (2006).
United States Pharmacopeia, The National Formulary, USP XII NF XVII, 1990.
Ziegler T. R., Pierce, G. F., and Herndon, D. N., 1997, International Symposium on Growth Factors and Wound Healing: Basic Science & Potential Clinical Applications (Boston, 1995, Serono Symposia USA), Publisher: Springer Verlag.

The invention claimed is:

1. A method for forming an elastic material, including:
providing a solution of tropoelastin monomers;
applying the solution to a surface; and
heating the solution on the surface to a temperature of from about 60° C. to about 200° C. at a pH of less than 8.5 and in the absence of a cross-linking agent to enable the tropoelastin monomers to bind to each other to form an elastic material that does not dissociate into tropoelastin monomers when the elastic material is contacted with an aqueous solution, wherein the elastic material is hard and glassy.

2. The method of claim 1, wherein the solution is heated to a temperature that is sufficient to enable the tropoelastin monomers to bind to each other to form an elastic material that does not dissociate into tropoelastin monomers when the elastic material is exposed to physiological conditions.

3. The method of claim 1, where in the solution is heated to a temperature that is sufficient to enable the tropoelastin monomers to bind to each other to form an elastic material that does not dissociate into tropoelastin monomers when the elastic material is contacted with an aqueous solution having a pH of from about 6.5 to 8.0.

4. The method of claim 1, where in the solution is heated to a temperature that is sufficient to enable the tropoelastin monomers to bind to each other to form an elastic material that does not dissociate into tropoelastin monomers when the elastic material is contacted with an aqueous solution having a temperature of from about 30 to about 45° C.

5. The method of claim 1, wherein the solution is heated to a temperature that is sufficient to enable the tropoelastin monomers to bind to each other to form an elastic material that does not dissociate into tropoelastin monomers when the elastic material is contacted with an aqueous solution having a salt concentration of about 75 mM to about 300 mM.

6. The method of claim 1, where in the surface is heated for heating of the solution of tropoelastin monomers.

7. The method of claim 1, where in the elastic material has a solvent content of up to about 50% (w/w) of the elastic material at the completion of the heating step.

8. The method of claim 1, where in the method includes increasing a concentration of tropoelastin monomers in the solution.

9. The method of claim 8, where in the concentration of tropoelastin monomers is increased by evaporating solvent from the solution of tropoelastin monomers.

10. The method of claim 9, wherein the solvent is evaporated from the solution when the solution of tropoelastin monomers is applied to the surface.

11. The method of claim 10, wherein the solvent is evaporated enabling concentration of the tropoelastin monomers as the solution is heated on the surface to a temperature enabling the tropoelastin monomers to bind to each other to form an elastic material that does not dissociate into tropoelastin monomers when the elastic material is contacted with an aqueous solution.

12. The method of claim 8, wherein the concentration of tropoelastin monomers is increased by separating tropoelastin monomers from solvent.

13. The method of claim 12, wherein the tropoelastin monomers are separated from the solvent by electrospinning of the tropoelastin monomers.

14. The method of claim 1, wherein the solution has a concentration of tropoelastin monomers from about 1 to 40% (w/v) when the solution is applied to the surface.

15. The method of claim 1, where in the solution includes coacervated tropoelastin monomers.

16. The method of claim 1, wherein the tropoelastin monomers contain hydrophilic and hydrophobic domains of tropoelastin.

17. The method of claim 1, where in the tropoelastin monomers have a sequence that has at least 90% sequence identity with an amino acid sequence of human tropoelastin across at least 50 consecutive amino acids.

18. The method of claim 1, where in the tropoelastin monomers are recombinant tropoelastin monomers having an amino acid sequence of a human tropoelastin isoform.

19. The method of claim 1, wherein the solution is applied to the surface by spraying the solution of tropoelastin monomers onto the surface.

20. The method of claim 1, wherein the surface is provided in the form of a die, mold or cast enabling the elastic material formed by the method to be shaped into a predefined shape.

21. The method of claim 1, wherein the solution is an aqueous solution.

22. A method of forming an elastic hydrogel, including:
forming an elastic material according to claim 1; and
contacting the elastic material with an aqueous solution.

23. The method of claim 1, wherein the heating is performed at a pH that is not an alkaline pH.

24. The method of claim 1, wherein the elastic material has an increased crystallinity after heating.

25. The method of claim 1, wherein the heating the solution comprises heating the solution to a temperature of from about 120° C. and about 180° C.

26. The method of claim 1, wherein the heating the solution is performed for at least two hours.

27. The method of claim 1, wherein the heating the solution is performed for between about 2 hours to about 16 hours.

28. The method of claim 1, wherein the heating the solution is performed for about 8 hours.

29. The method of claim 28, wherein the elastic material has an increased crystallinity after heating.

30. The method of claim 1, wherein the solution of tropoelastin monomers comprises a concentration from about 10 mg/ml to about 350 mg/ml.

31. The method of claim 1, wherein the solution of tropoelastin monomers comprises a concentration of about 100 mg/ml.

32. A method for forming an elastic material, the method comprising: providing a solution of tropoelastin monomers;
applying the solution to a surface; and
heating the solution on the surface to a temperature of from about 60° C. to about 200° C. in the absence of a cross-linking agent to enable the tropoelastin monomers to bind to each other to form a hard, elastic material that does not dissociate into tropoelastin monomers when the elastic material is contacted with an aqueous solution.

33. A method for forming an elastic material, the method comprising: providing a solution of tropoelastin monomers;
applying the solution to a surface; and
heating the solution on the surface to a temperature of from about 60° C. to about 200° C. in the absence of a cross-linking agent to enable the tropoelastin monomers to bind to each other to form a glassy, elastic material that does not dissociate into tropoelastin monomers when the elastic material is contacted with an aqueous solution.

34. The method of claim 33, wherein the elastic material has an increased crystallinity after heating.

35. A method for forming an elastic material, the method comprising: providing a solution of tropoelastin monomers;
applying the solution to a surface; and
heating the solution on the surface to a temperature of from about 60° C. to about 200° C. in the absence of a cross-linking agent to enable the tropoelastin monomers to bind to each other to form a glassy, elastic material that does not substantially dissociate into tropoelastin monomers when the elastic material is contacted with an aqueous solution.

36. The method of claim 35, wherein the solution on the surface is heated to a temperature of from about 130° C. to about 170° C.

37. The method of claim 35, wherein the solution on the surface is heated to a temperature of from about 140° C. to about 160° C.

38. The method of claim 35, wherein the solution on the surface is heated to a temperature of about 160° C.

* * * * *

SEQUENCE LISTING

<160> NUMBER OF SEQ ID NOS: 31

<210> SEQ ID NO 1
<211> LENGTH: 5
<212> TYPE: PRT
<213> ORGANISM: Artificial Sequence
<220> FEATURE:
<223> OTHER INFORMATION: Peptide sequence

<400> SEQUENCE: 1

Gly Val Gly Val Pro
1               5

```
<210> SEQ ID NO 2
<211> LENGTH: 4
<212> TYPE: PRT
<213> ORGANISM: Artificial Sequence
<220> FEATURE:
<223> OTHER INFORMATION: Peptide sequence

<400> SEQUENCE: 2

Gly Gly Val Pro
1

<210> SEQ ID NO 3
<211> LENGTH: 6
<212> TYPE: PRT
<213> ORGANISM: Artificial Sequence
<220> FEATURE:
<223> OTHER INFORMATION: Peptide sequence

<400> SEQUENCE: 3

Gly Val Gly Val Ala Pro
1               5

<210> SEQ ID NO 4
<211> LENGTH: 9
<212> TYPE: PRT
<213> ORGANISM: Artificial Sequence
<220> FEATURE:
<223> OTHER INFORMATION: Peptide sequence

<400> SEQUENCE: 4

Ala Ala Ala Lys Ala Ala Lys Ala Ala
1               5

<210> SEQ ID NO 5
<211> LENGTH: 18
<212> TYPE: PRT
<213> ORGANISM: Artificial Sequence
<220> FEATURE:
<223> OTHER INFORMATION: Peptide sequence

<400> SEQUENCE: 5

Gly Gly Val Pro Gly Ala Ile Pro Gly Gly Val Pro Gly Gly Val Phe
1               5                   10                  15

Tyr Pro

<210> SEQ ID NO 6
<211> LENGTH: 9
<212> TYPE: PRT
<213> ORGANISM: Artificial Sequence
<220> FEATURE:
<223> OTHER INFORMATION: Peptide sequence

<400> SEQUENCE: 6

Gly Val Gly Leu Pro Gly Val Tyr Pro
1               5

<210> SEQ ID NO 7
<211> LENGTH: 7
<212> TYPE: PRT
<213> ORGANISM: Artificial Sequence
<220> FEATURE:
<223> OTHER INFORMATION: Peptide sequence

<400> SEQUENCE: 7

Gly Val Pro Leu Gly Tyr Pro
1               5
```

<210> SEQ ID NO 8
<211> LENGTH: 13
<212> TYPE: PRT
<213> ORGANISM: Artificial Sequence
<220> FEATURE:
<223> OTHER INFORMATION: Peptide sequence

<400> SEQUENCE: 8

Pro Tyr Thr Thr Gly Lys Leu Pro Tyr Gly Tyr Gly Pro
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Peptide sequence

<400> SEQUENCE: 9

Gly Gly Val Ala Gly Ala Ala Gly Lys Ala Gly Tyr Pro
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Peptide sequence

<400> SEQUENCE: 10

Thr Tyr Gly Val Gly Ala Gly Gly Phe Pro
1               5                   10

<210> SEQ ID NO 11
<211> LENGTH: 5
<212> TYPE: PRT
<213> ORGANISM: Artificial Sequence
<220> FEATURE:
<223> OTHER INFORMATION: Peptide sequence

<400> SEQUENCE: 11

Lys Pro Leu Lys Pro
1               5

<210> SEQ ID NO 12
<211> LENGTH: 12
<212> TYPE: PRT
<213> ORGANISM: Artificial Sequence
<220> FEATURE:
<223> OTHER INFORMATION: Peptide sequence

<400> SEQUENCE: 12

Ala Asp Ala Ala Ala Ala Tyr Lys Ala Ala Lys Ala
1               5                   10

<210> SEQ ID NO 13
<211> LENGTH: 9
<212> TYPE: PRT
<213> ORGANISM: Artificial Sequence
<220> FEATURE:
<223> OTHER INFORMATION: Peptide sequence

<400> SEQUENCE: 13

Gly Ala Gly Val Lys Pro Gly Lys Val
1               5

```
<210> SEQ ID NO 14
<211> LENGTH: 9
<212> TYPE: PRT
<213> ORGANISM: Artificial Sequence
<220> FEATURE:
<223> OTHER INFORMATION: Peptide sequence

<400> SEQUENCE: 14

Gly Ala Gly Val Lys Pro Gly Lys Val
1               5

<210> SEQ ID NO 15
<211> LENGTH: 9
<212> TYPE: PRT
<213> ORGANISM: Artificial Sequence
<220> FEATURE:
<223> OTHER INFORMATION: Peptide sequence

<400> SEQUENCE: 15

Thr Gly Ala Gly Val Lys Pro Lys Ala
1               5

<210> SEQ ID NO 16
<211> LENGTH: 7
<212> TYPE: PRT
<213> ORGANISM: Artificial Sequence
<220> FEATURE:
<223> OTHER INFORMATION: Peptide sequence

<400> SEQUENCE: 16

Gln Ile Lys Ala Pro Lys Leu
1               5

<210> SEQ ID NO 17
<211> LENGTH: 6
<212> TYPE: PRT
<213> ORGANISM: Artificial Sequence
<220> FEATURE:
<223> OTHER INFORMATION: Peptide sequence

<400> SEQUENCE: 17

Val Ala Pro Gly Val Gly
1               5

<210> SEQ ID NO 18
<211> LENGTH: 5
<212> TYPE: PRT
<213> ORGANISM: Artificial Sequence
<220> FEATURE:
<223> OTHER INFORMATION: Peptide sequence

<400> SEQUENCE: 18

Val Pro Gly Val Gly
1               5

<210> SEQ ID NO 19
<211> LENGTH: 12
<212> TYPE: PRT
<213> ORGANISM: Artificial Sequence
<220> FEATURE:
<223> OTHER INFORMATION: Peptide sequence

<400> SEQUENCE: 19

Ala Ala Ala Ala Ala Ala Ala Lys Ala Ala Ala Lys
1               5                   10
```

```
<210> SEQ ID NO 20
<211> LENGTH: 22
<212> TYPE: PRT
<213> ORGANISM: Artificial Sequence
<220> FEATURE:
<223> OTHER INFORMATION: Peptide sequence

<400> SEQUENCE: 20

Ala Ala Ala Ala Ala Ala Ala Ala Ala Ala Lys Ala Ala Lys Tyr Gly
1               5                   10                  15

Ala Ala Ala Gly Leu Val
            20

<210> SEQ ID NO 21
<211> LENGTH: 16
<212> TYPE: PRT
<213> ORGANISM: Artificial Sequence
<220> FEATURE:
<223> OTHER INFORMATION: Peptide sequence

<400> SEQUENCE: 21

Glu Ala Ala Ala Lys Ala Ala Ala Lys Ala Ala Lys Tyr Gly Ala Arg
1               5                   10                  15

<210> SEQ ID NO 22
<211> LENGTH: 17
<212> TYPE: PRT
<213> ORGANISM: Artificial Sequence
<220> FEATURE:
<223> OTHER INFORMATION: Peptide sequence

<400> SEQUENCE: 22

Glu Ala Gln Ala Ala Ala Ala Ala Lys Ala Ala Lys Tyr Gly Val Gly
1               5                   10                  15

Thr

<210> SEQ ID NO 23
<211> LENGTH: 17
<212> TYPE: PRT
<213> ORGANISM: Artificial Sequence
<220> FEATURE:
<223> OTHER INFORMATION: Peptide sequence

<400> SEQUENCE: 23

Ala Ala Ala Ala Ala Lys Ala Ala Ala Lys Ala Ala Gln Phe Gly Leu
1               5                   10                  15

Val

<210> SEQ ID NO 24
<211> LENGTH: 29
<212> TYPE: PRT
<213> ORGANISM: Artificial Sequence
<220> FEATURE:
<223> OTHER INFORMATION: Peptide sequence

<400> SEQUENCE: 24

Gly Gly Val Ala Ala Ala Ala Lys Ser Ala Ala Lys Val Ala Ala Lys
1               5                   10                  15

Ala Gln Leu Arg Ala Ala Ala Gly Leu Gly Ala Gly Ile
            20                  25

<210> SEQ ID NO 25
<211> LENGTH: 15
<212> TYPE: PRT
<213> ORGANISM: Artificial Sequence
```

```
<220> FEATURE:
<223> OTHER INFORMATION: Peptide sequence

<400> SEQUENCE: 25

Gly Ala Leu Ala Ala Ala Lys Ala Ala Lys Tyr Gly Ala Ala Val
1               5                   10                  15

<210> SEQ ID NO 26
<211> LENGTH: 14
<212> TYPE: PRT
<213> ORGANISM: Artificial Sequence
<220> FEATURE:
<223> OTHER INFORMATION: Peptide sequence

<400> SEQUENCE: 26

Ala Ala Ala Ala Ala Ala Ala Lys Ala Ala Ala Lys Ala Ala
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Peptide sequence

<400> SEQUENCE: 27

Ala Ala Ala Ala Lys Ala Ala Lys Tyr Gly Ala Ala
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Peptide sequence

<400> SEQUENCE: 28

Cys Leu Gly Lys Ala Cys Gly Arg Lys Arg Lys
1               5                   10

<210> SEQ ID NO 29
<211> LENGTH: 6
<212> TYPE: PRT
<213> ORGANISM: Artificial Sequence
<220> FEATURE:
<223> OTHER INFORMATION: Peptide sequence
<220> FEATURE:
<221> NAME/KEY: misc_feature
<222> LOCATION: (2)..(2)
<223> OTHER INFORMATION: Xaa can be any naturally occurring amino acid

<400> SEQUENCE: 29

Val Xaa Pro Gly Val Gly
1               5

<210> SEQ ID NO 30
<211> LENGTH: 6
<212> TYPE: PRT
<213> ORGANISM: Artificial Sequence
<220> FEATURE:
<223> OTHER INFORMATION: Peptide sequence
<220> FEATURE:
<221> NAME/KEY: misc_feature
<222> LOCATION: (2)..(2)
<223> OTHER INFORMATION: Xaa can be any naturally occurring amino acid

<400> SEQUENCE: 30

Glx Xaa Pro Gly Glx Gly
```

```
<210> SEQ ID NO 31
<211> LENGTH: 10
<212> TYPE: PRT
<213> ORGANISM: Artificial Sequence
<220> FEATURE:
<223> OTHER INFORMATION: Peptide sequence
<220> FEATURE:
<221> NAME/KEY: misc_feature
<222> LOCATION: (2)..(2)
<223> OTHER INFORMATION: Xaa can be any naturally occurring amino acid

<400> SEQUENCE: 31

Val Xaa Pro Ile Leu Val Val Ile Leu Val
1               5                   10
```